United States Patent
King et al.

(10) Patent No.: US 6,911,460 B2
(45) Date of Patent: Jun. 28, 2005

(54) ANTIVIRAL AGENTS AND METHODS OF TREATING VIRAL INFECTIONS

(75) Inventors: Ivan C. King, North Haven, CT (US); Terrance W. Doyle, Killingworth, CT (US); Mario Sznol, Woodbridge, CT (US); Alan C. Sartorelli, Woodbridge, CT (US); Yung-Chi Cheng, Woodbridge, CT (US)

(73) Assignees: Vion Pharmaceuticals, Inc., New Haven, CT (US); Yale University, New Haven, CT (US)

( * ) Notice: Subject to any disclaimer, the term of this patent is extended or adjusted under 35 U.S.C. 154(b) by 0 days.

(21) Appl. No.: 10/126,050

(22) Filed: Apr. 18, 2002

(65) Prior Publication Data

US 2002/0188011 A1 Dec. 12, 2002

Related U.S. Application Data

(60) Provisional application No. 60/285,559, filed on Apr. 20, 2001.

(51) Int. Cl.$^7$ .................... A61K 31/44; A61K 31/175; A61K 31/70; A61K 31/522
(52) U.S. Cl. .................... 514/352; 514/45; 514/51; 514/581; 514/582; 514/263.37
(58) Field of Search .................. 514/352, 353, 514/45, 51, 581, 582, 263.37, 584, 583.582

(56) References Cited

U.S. PATENT DOCUMENTS

| | | | | |
|---|---|---|---|---|
| 5,767,134 A | * | 6/1998 | Li et al. | 514/353 |
| 6,165,484 A | | 12/2000 | Raad et al. | |
| 6,248,782 B1 | * | 6/2001 | Elford et al. | 514/512 |
| 6,458,816 B1 | * | 10/2002 | Doyle et al. | 514/353 |

FOREIGN PATENT DOCUMENTS

| WO | WO 99/39732 | 8/1999 |
|---|---|---|
| WO | WO 01/10454 | 2/2001 |

OTHER PUBLICATIONS

Spingarn and Sartorelli. "Synthesis and Evaluation of the Thiosemicarbazone, Dithiocarbazonate, and 2'–Pyrazinylhydrazone of Pyrazinecarboxaldehyde as Agents for the Treatment of Iron Overload" *Journal of Medicinal Chemistry*, 22(11): p. 1314–1316, 1979.

* cited by examiner

*Primary Examiner*—Shengjun Wang
(74) *Attorney, Agent, or Firm*—Henry D. Coleman; R. Neil Sudol; William J. Sapone

(57) ABSTRACT

The present invention relates to methods of treating viral or fungal infections using 3-aminopyridine-2-carboxyaldehyde thiosemicarbazone (3-AP) and 3-amino-4-methylpyridine-2-carboxaldehyde thiosemicarbazone (3-AMP) and its prodrug forms and to pharmaceutical compositions comprising these compounds.

4 Claims, 4 Drawing Sheets

ANTIVIRAL AGENTS AND METHODS OF TREATING VIRAL INFECTIONS

RELATED APPLICATIONS

This application claims the benefit of provisional patent application 60/285,559 filed Apr. 20, 2001.

FIELD OF THE INVENTION

The present invention relates to methods of treating viral infections using 3-aminopyridine-2-carboxyaldehyde thiosemicarbazone (3-AP, Triapine™) and 3-amino-4-methylpyridine-2-carboxaldehyde thiosemicarbazone (3-AMP) and their prodrug forms and to pharmaceutical compositions comprising these compounds. Combination therapy with other antiviral agents, in particular, nucleoside antiviral agents, represents another aspect of the present invention.

BACKGROUND

Triapine is a ribonucleotide reductase (RNR) inhibitor that reduces the cellular pool of DNA precursors (dNTPs) by interfering with their de novo synthesis (Cory et al., (1994) *Biochem. Pharmacol.* 48, 335–44). Depletion of dNTPs resulted in inhibition of DNA synthesis. Triapine was first developed as an anti-cancer agent for its action against the growth of tumor cells both in vitro and in vivo (Liu et al., (1992) *J. Med. Chem.* 35, 3672–77). It has recently been shown that concentration of Triapine reached 1.0 micromolar in cancer patients receiving a 96-hour infusion of Triapine at a dose of 96 mg/mm2 (Modiano et al., *Proc. Am. Assoc. Cancer Res.*, 42, 834, 2001). The mechanism of action of Triapine is similar to that of another anti-cancer agent, hydroxyurea, which has been approved for treatment of cancers in humans.

Recently, hydroxyurea, another known RNR inhibitor, was shown to have synergistic effects against HIV-infected cells (human immunodeficiency viruses, the causative agents of AIDS) when combined with 2',3'-dideoxyinosine (DDI) (Gao et al., (1998) *Biochem. Pharmacol.* 56, 105–12). The mechanism of action is unknown, but may be due to the depletion of dNTPs in cells treated with hydroxyurea.

3-AP and 3-AMP, like other thiosemicarbazone analogs of this class (Springam and Sartorelli, *J. Med. Chem.* (1979) 22, 1314–6), have very strong iron binding affinity and are capable of removing iron from ferritin. Iron is required RNR activity and for normal physiological function of organisms and iron deprivation inhibits proliferation of protozoa (Merali et al., *Antimicrob. Agents Chemother.* (1996) 40, 1298–1300), bacteria (Lowy et al., *Antimicrob. Agents Chemother.* (1984) 25, 375–6), fungi (Newman et al., *Antimicrob. Agents Chemother.* (1995) 39, 1824–9; Shulman et al., *Arzneimittelforschung* (1972) 22, 154–8; Kerbs et al., *Sabouraudia* (1979), 17, 241–50), and viruses (Dai et al., *Virology* (1994) 205, 210–6; Cinatl et al., *Antiviral Res.* (1994) 25, 73–77; Bayraktar et al., *J. Viral Hepat.* (1996) 3, 129–35; Martelius et al, *Transplantation* (1999) 15, 1753–61; Georgiou et al, *J. Infect. Dis.* (2000) 181, 484–90). In addition to depletion of intracellular dNTP pools, that 3-AP inhibits viral dissemination could be mediated through its iron chelating properties (Chouteau et al., *J. Hepatol.* (2001) 34, 108–13; Georgiou et al, *J. Infect. Dis.* (2000) 181, 484–90; Bayraktar et al., *J. Viral Hepat.* (1996) 3, 129–35; Conti et al., *Boll. Ist. Sieroter Milan* (1990) 69, 431–6).

3-AP, because of its strong iron-chelating property, can be used to remove excessive tissue iron in sickle cell disease patients who require regular blood transfusion (Cohen and Martin, *Semin. Hematol.* (2001) 38(Suppl. 1), 69–72). As a potent inhibitor of RNR, 3-AP could also be used for the treatment of psoriasis (Smith, *Clin. Exp. Dermatol.* (1999) 24, 2–6).

Chronic HBV (hepatitis B virus) infection remains a therapeutic challenge for clinicians. The recent development of lamivudine has provided new hope in the therapy of chronic hepatitis B. However, due to the slow kinetics of viral clearance and the spontaneous genetic variability of HBV, lamivudine therapy is associated with the selection of drug resistant mutants in up to 50% of patients after 3 years of therapy. It is therefore important to continue research to develop new anti-HBV strategies using in vitro and in vivo evaluation in experimental models of HBV replication.

Herpes simplex virus (HSV) encodes a RNR which is similar to the one encoded by mammalian cells. HSV replication does not require the expression of viral RNR in exponentially growing cells but is required for viral replication in quiescent cells (Goldstein and Weller, (1988) *Virol.* 166, 1–51). Duan et al., *Antimicrob. Agents Chemother.* (1998) 42, 1629–35, showed that the RNR inhibitor BILD1633 SE in combination with acyclovir had activity against acyclovir-resistant HSV strains.

Recently, flavivirus infections, including West Nile virus infections, have become increasingly frequent in the United States. The flaviviruses are agents of infectious disease which predominate in East, Southeast and South Asia and Africa, although they may be found in other parts of the world as well. Japanese encephalitis virus is the causative agent of Japanese encephalitis (JE). The mortality rate from JE is rather high and the disease brings heavy sequelae. Although found in Japan, the disease has spread to other parts of Asia and is now found predominantly outside of Japan, primarily in South and Southeast Asia.

Dengue viruses are causative agents of dengue fever/dengue hemorrhagic fever. Infection with dengue viruses is a major public health problem in tropical countries, especially in Southeast Asia and the Western Pacific, but dengue viruses may also be found in the Americas. As the dengue virus is transmitted to humans via the Aedes aegypti mosquito, it is not unexpected that tropical and subtropical countries, in particular, those in Southeast Asia, are highly endemic for dengue.

Viral replication requires dNTPs, and depletion of intracellular dNTPs by Triapine may prevent viruses from multiplying. In addition, this new strategy may be used in combination with other anti-viral agents to treat, or to prevent or delay the development of drug resistant mutants.

OBJECTS OF THE INVENTION

It is an object of the invention to provide novel combination pharmaceutical compositions for treating viral infections in patients.

It is another object of the invention to provide novel methods for reducing viral growth, elaboration and replication and for treating viral infections in patients.

It is also an object of the invention to provide methods for treating fungal infections in patients.

Any one or more of these and/or other objects of the present invention may be readily gleaned from a review of the description of the present invention.

SUMMARY OF THE INVENTION

Figure 1:
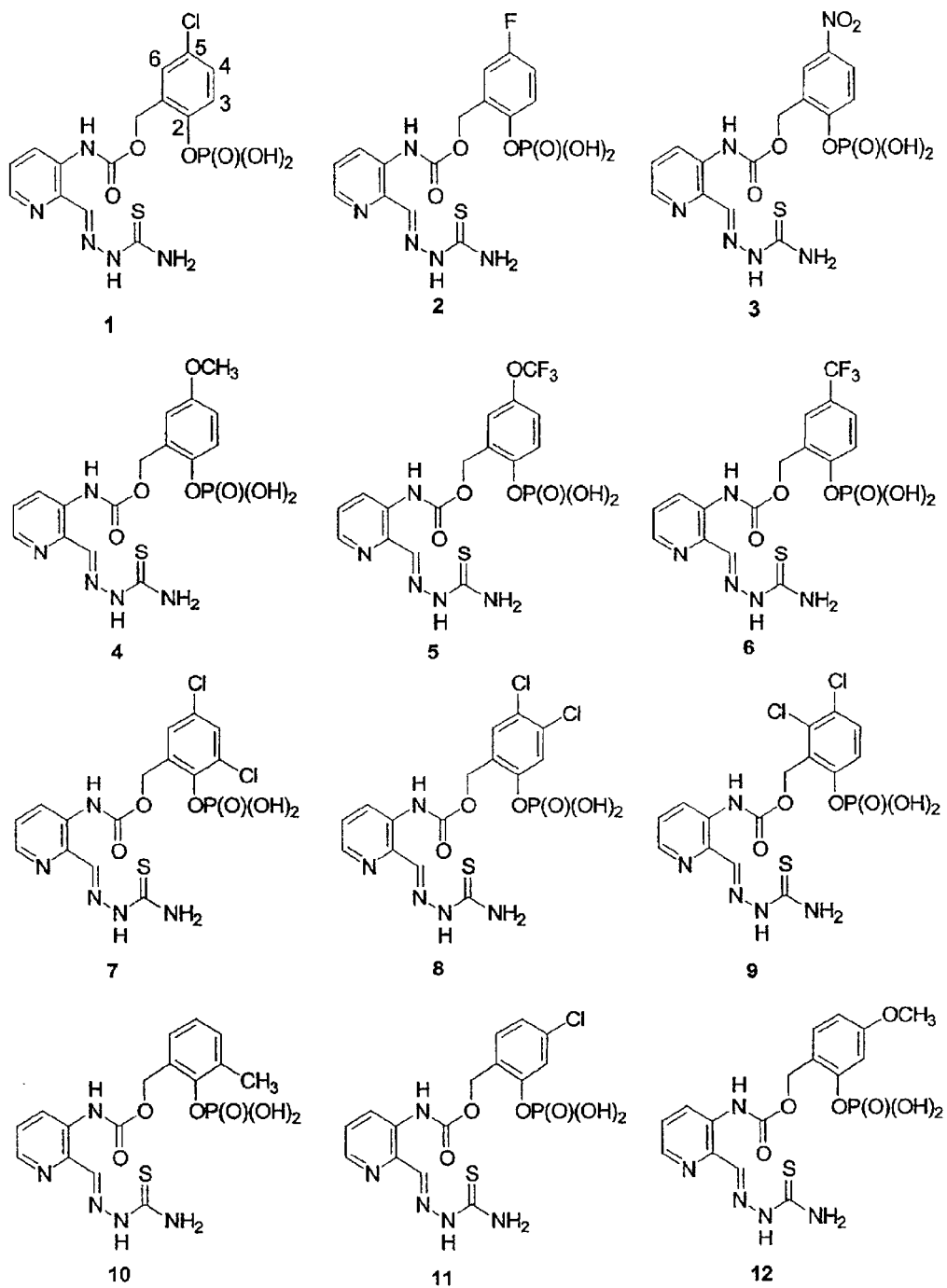
FIG. 1 is a representation of certain chemical embodiments according to the present invention.

The present invention relates to methods for inhibiting the growth, replication or elaboration of a virus population or for treating a variety of virus infections, including, for example, human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, said method comprising administering an anti-viral effective amount of a composition according to the present invention to a patient in need thereof to treat, prevent or reduce the likelihood of contracting a viral infection.

The present invention therefore relates to a method of treating inhibiting the growth, replication and/or the elaboration of a viral population or a viral infection in a patient, comprising administration to said patient an effective amount of a compound according to the structure:

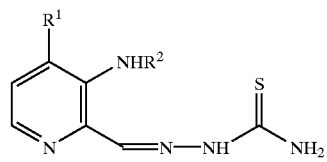

Where $R^1$ is H or a $C_1$–$C_3$ alkyl group, preferably H or $CH_3$; $R^2$ is H or $CO_2R^3$; $R^3$ is CHRR' or

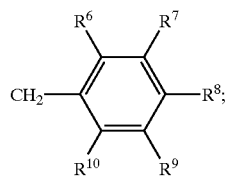

where R is H, $CH_3$, $CH_2CH_3$, $CH_2CH_2CH_3$, i-propyl; R' is a free acid phosphate, phosphate salt or S—S—R" group; R" is $CH_2CH_2NHR^4$, $CH_2CH_2OH$, $CH_2COOR^5$, ortho- or para-substituted $C_1$–$C_3$ alkylphenyl or ortho or para nitrophenyl; $R^4$ is H or a $C_1$–$C_{18}$ acyl group (preferably, a $C_1$–$C_4$ group), benzoyl, or a substituted benzoyl group; $R^5$ is H, a $C_1$–$C_{18}$ alkyl group (preferably, a $C_1$–$C_3$ group), phenyl, substituted phenyl, benzyl, or a substituted benzyl group; $R^6$, $R^7$, $R^8$, $R^9$ and $R^{10}$ are independently selected from H, a free acid phosphate, a phosphate salt, or an S—S—R" group, a $C_1$–$C_3$ alkyl group, F, Cl, Br, I, $OCH_3$, $OCF_3$, $CF_3$, $NO_2$, CN, $SO_2CF_3$, $SO_2CH_3$, $COOCH_3$, $SF_5$, $COCH_3$, $NH_2$, $N(CH_3)_2$, $SCH_3$ or OH;
With the proviso that when any two of $R^6$, $R^7$, $R^8$, $R^9$ and $R^{10}$ are other than H, the other of $R^6$, $R^7$, $R^8$, $R^9$ and $R^{10}$ are H, and with the proviso that no more than one of $R^6$, $R^7$, $R^8$, $R^9$ and $R^{10}$ is a free acid phosphate, a phosphate salt or S—S—R".

In preferred aspects of the present invention, $R^6$, $R^8$ or $R^{10}$ is a free acid phosphate or a phosphate salt. In other preferred aspects of the present invention, $R^6$ is a free acid phosphate or phosphate salt and the other of $R^7$, $R^8$, $R^9$ and $R^{10}$ are H. In still other aspects of the present invention $R^1$ and $R^2$ are both H.

The invention provides methods of use relating to treatment of infections caused by viruses, including, for example, human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses. The method includes the use of prodrug forms of 3-AP and 3-AMP as otherwise described herein for the treatment of viral infections.

In alternative embodiments, compounds according to the present invention may be used to treat fungal infections including, for example, infections caused by *Piedraia hortae, Trichosporon beigelii, Malassezia furfur, Epidermophyton* spp., *Microsporum* spp., *Trichophyton* spp., *Blastomyces dermatitidis, Coccidioides immitis, Cryptococcus neoformans, Histoplasma capsulatum, Aspergillus* spp. and *Candida albicans.* Methods of treating fungal infections comprising administering an anti-fungal effective amount of one or more of 3-AP, 3-AMP or one of its prodrugs as otherwise described herein.

Compositions according to the present invention may be used alone or in combination with reverse transcriptase inhibitors, protease inhibitors, other immunomodulators, all for the treatment of HIV infections, as well as other viral infections. The invention also provides methods of use for the treatment of HBV infections by combining one or more compounds according to the present invention along with reverse trancriptase inhibitors, or interferon, or both. The invention also provides a method for the treatment of HSV infection by combining an effective amount of one or more of the compositions as described above with one or more anti-HSV agents such as acyclovir, DDI and D4T in amounts effective to treat the viral infection. Without being limited by way of theory, it is believed that the use of the presently described compounds exhibit their anti-viral activity primarily through inhibition of cellular and viral RNR and/or chelation of divalent metal ions such as iron, among others. Use of compositions in combination therapy which inhibit viruses in a manner other than through RNR are particularly preferred as they often provide synergistic anti-viral activity in combination with 3-AP ($R^1$ and $R^2$ are H), 3-AMP ($R^1$ is $CH_3$ and $R^2$ is H) and prodrug compositions according to the present invention.

DETAILED DESCRIPTION OF THE INVENTION

The following terms shall be used throughout the specification to describe the present invention.

The term "patient" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

The term "virus" shall be used to describe all types of viruses, the growth or replication of which may be inhibited or disease states of which may be treated using one or more methods according to the present invention. Viruses which may be treated according to the present invention include, for example, human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others.

The term "human immunodeficiency virus" shall be used to describe human immunodeficiency virus (HIV) and its infections, which term shall be used to embrace both human immunodeficieny virus 1 (HIV-1) and human immunodeficiency virus 2 (HIV-2).

The term "human T-cell leukemia virus" shall be used to describe human T-cell leukemia virus and its infections, which term shall be used to embrace both human T-cell leukemia virus 1 (HTLV-1) and human T-cell leukemia virus 2 (HTLV-2).

The term "Hepatitis B Virus" (HBV) is used to describe the virus (serum hepatitis virus) which produces viral hepatitis type B in humans. This is a viral disease with a long incubation period (about 50 to 160 days) in contrast to Hepatitis A virus (infectious hepatitis virus) which has a short incubation period. The virus is usually transmitted by injection of infected blood or blood derivatives or merely by use of contaminated needles, lancets or other instruments. Clinically and pathologically, the disease is similar to viral hepatitis type A; however, there is no cross-protective immunity. Viral antigen (HBAg) is found in the serum after infection.

The term "Hepatitis C Virus" or (HCV) is used throughout the specification to describe the hepatitis virus which is the causative agent of non-A, non-B hepatitis. The disease in the acute stage is, in general, milder than hepatitis B, but a greater proportion of such infections become chronic.

The term "Epstein-Barr virus" (EBV) is used throughout the specification to describe a herpetovirus found in cell cultures of Burkitt's lymphoma. EBV is the causative agent in infectious mononucleosis, as well as in a number of other related conditions/disease states, including EBV-associated lymphomas.

The term "Varicella-Zoster virus" (VZV) is used to describe *Herpesvirus varicellae*, also known as chicken pox or herpes zoster. Varicella results from a primary infection with the virus; herpes zoster results from secondary invasion by the same or by reactivation of infection which in many instances may have been latent for a number of years. Both the primary and secondary infections of VZV may be treated using compositions according to the present invention.

The term "respiratory syncytial virus" (RSV) is used throughout the specification to describe an RNA-containing virus of the genus *Pneumovirus* that causes minor respiratory infection with rhinitis and cough in adults, but is capable of causing bronchitis and bronchopneumonia in young children. The virus is named for the tendency to form syncytia in tissue culture.

The term "adenovirus" is used throughout the specification to describe a virus of the family adenoviridae which are doublestranded DNA-containing viruses, which infect mammals and birds. The virion is 70 to 90 mn in diameter and is naked (has no envelope). The virus develops in nuclei of infected cells; isolation requires tissue cultures since laboratory animals are not susceptible to apparent infection. The family includes two genera, *Mastadenovirus* and *Acviadenovirus*.

The term "Human Herpes Virus 8" (HHV-8) is used throughout the specification to describe a herpetovirus which is believed to be the causative agent of Kaposi's sarcoma in AIDS patients.

The term "Human Papilloma Virus" (HPV) is used throughout the specification to describe a virus which causes genital warts. Also known as infectious warts virus, HPV is a universal, common, often recurrent viral infection with a large number of serotypes. HPV infection can lead to the formation of genital warts which can, in turn, lead to genital and/or cervical cancer. Genital warts caused by HPV types 1, 2, 6, 11, 16 and 18 are generally transmitted sexually and are often associated with cervical and/or genital cancer. HPV may mature to produce a papillary tumor or wart, which is a circumscribed benign epithelial tumor projecting from the surrounding surface. It is generally a benign epithelial neoplasm consisting of villous or arborescent outgrowths of fibrovascular stroma covered by neoplastic cells.

The term "flavivirus" is used throughout the specification to describe viruses belonging to the genus *Flavivirus* of the family Togaviridae. According to virus taxonomy, about 50 viruses including Hepatitis C virus (HCV), Yellow Fever virus, Dengue Virus, Japanese Encephalitis virus, West Nile virus and related flaviviruses are members of this genus. The viruses belonging to the genus *Flavivirus* are simply called flaviviruses. These viruses were formerly classified as group B arboviruses. The flaviviruses are agents of infectious disease and predominate in East, Southeast and South Asia and Africa, although they may be found in other parts of the world as well.

The term "Yellow Fever virus" is used to describe the *flavivirus* which is the causative agent of yellow fever. Yellow fever is a tropical mosquito-borne viral hepatitis, due to Yellow Fever virus (YFV), with an urban form transmitted by *Aedes aegypti*, and a rural, jungle or sylvatic form from tree-dwelling mammals by various mosquitos of the *Haemagogus* species complex. Yellow fever is characterized clinically by fever, slow pulse, albuminuria, jaundice, congesion of the face and hemorrhages, especially hematemesis ("black vomit"). It is fatal in about 5–10% of the cases.

The term "Dengue virus" is used throughout the specification to descibe the flavivirus which is the causative agent(s) of dengue fever/dengue hemorrhagic fever. Dengue is a disease of tropical and subtropical regions occurring epidemically and caused by Dengue virus, one of a group of arboviruses which causes the hemorrhagic fever syndrome. Four grades of severity are recognized: grade I: fever and constitutional symptoms, grade II: grade I plus spontaneous bleeding (of skin, gums or gastrointestinal tract), grade III: grade II plus agitation and circulatory failure and grade IV: profound shock. The disease is transmitted by a mosquito of the genus *Aedes* (generally *A. aegyptii*, but frequently, *A. albopictus*). Also called Aden, bouquet, breakbone, dandy, date, dengue (hemorrhagic) or polka, solar fever, stiffneck fever, scarlatina rheumatica or exanthesis arthorosia. "Hemorrhagic dengue" is a more pathogenic epidemic form of dengue which has erupted in a number of epidemic outbreaks in the Pacific region in recent years.

The term "West Nile virus" is used to describe the flavivirus which is the causative agent of West Nile fever, a disease characterized by headache, fever, masculopapular rash, myalgia, lymphadenopathy and leukopenia. The virus is spread by *Culex* mosquitoes from a reservoir in birds. Although in the past, West Nile virus infections had been considered virtually nonexistent in the United States, recent developments have suggested that West Nile and other flavivirus infections will appear with greater regulatory in the future in the United States.

The term fungus shall mean "fungus" as that term is generally known in the art. Fungal infections which may be treated using 3-AP, 3-AMP and their prodrug forms alone or in combination with other anti-fungal agents including, for example infections caused by *Piedraia hortae, Trichosporon beigelii, Malassezia furfur, Epidermophyton* spp., *Microsporum* spp., *Trichophyton* spp., *Blastomyces dermatitidis, Coccidioides immitis, Cryptococcus neoformans, Histoplasma capsulatum, Aspergillus* spp., *Candida albicans.*

The term "anti-fungal agent" shall used to describe a compound which may be used to treat a fungus infection other than 3-AP, 3-AMP or prodrugs of 3-AP and 3-AMP according to the present invention. Anti-fungal agents according to the present invention include, for example, terbinafine, fluconazole, itraconazole, posaconazole, clotrimazole, griseofulvin, nystatin, tolnaftate, caspofungin, amphotericin B, liposomal amphotericin B, and amphotericin B lipid complex.

The term "pharmaceutically acceptable salt" is used throughout the specification to describe a salt form of one or more of the compositions (and in particularly preferred aspects according to the present invention, phosphate salts) herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids and free acid phosphate containing compositions according to the present invention.

The term "inhibitory effective concentration" or "inhibitory effective amount" is used throughout the specification to describe concentrations or amounts of compounds according to the present invention which substantially or significantly inhibit the growth or replication of susceptible viruses, especially including human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others. This term also refers to amounts of concentrations of compounds (whether 3-AP, 3-AMP or its prodrugs or more traditional anti-fungal agents as described in the present specification) which inhibit the growth of fungi.

The term "therapeutic effective amount" or "therapeutically effective amount" is used throughout the specification to describe concentrations or amounts of compounds according to the present invention which are therapeutically effective in treating viruses or fungi according to the present invention.

The term "preventing effective amount" is used throughout the specification to describe concentrations or amounts of compounds according to the present invention which are prophylactically effective in preventing, reducing the likelihood of infection or delaying the onset of infections in patients caused by human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others. This term shall also be used to describe amounts or concentrations of anti-fungal agents which are prophylactically effective in preventing, reducing the likelihood or delaying the onset of a fungal infection.

The term "effective amount" shall mean an amount or concentration of a compound according to the present invention which is effective within the context of its administration or use, including, for example, the treatment or prevention of viral and/or fungal infections.

The term "coadministration" or "combination therapy" is used to describe a therapy in which at least two active compounds in effective amounts are used to treat a viral or fungal infection at the same time. Although the term coadministration preferably includes the administration of two active compounds to the patient at the same time, it is not necessary that the compounds be administered to the patient at the same time, although effective amounts of the individual compounds will be present in the patient at the same time.

The term "alkyl" is used throughout the specification to describe a hydrocarbon radical containing between one and three carbon units. Alkyl groups for use in the present invention include linear or branched-chain groups, such as propyl and isopropyl.

The present invention relates to the use of 3-AP and 3-AMP, including their prodrug forms, as otherwise described herein for the inhibition of viral infections and the treatment of viral diseases in animals, including humans. Viruses which can be treated by the present invention include, for example, human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others.

The present invention also describes the use of 3-AP and 3-AMP and its prodrug forms in combination with other agents which may be used to treat viral infections and to prevent a viral infection or reduce the likelihood that an exposure of an animal to a virus will result in a viral infection in that animal. Another aspect of the present invention relates to combination therapy with at least one compound according to the present invention, in combination with at least one additional anti-viral agent which inhibits viruses by a mechanism other than by inhibition of viral RNR, which combination therapy produces synergistic inhibition of viral infections.

The present invention may be used in the treatment of HIV infections. For example, compositions according to the present invention may be combined with other anti-HIV agents, especially including, for example, D4T, DDI, AZT, lamivudine, Beta-L-5-Fluoro-2',3'-dideoxydidehydrocytidine (β-LFd4C), Beta-L-5-Fluoro-2', 3'-dideoxycytidine (β-LFddC), Beta-L-2',3'-dideoxydidehydrocytidine (β-Ld4C) or other nucleoside anti-HIV agents for the treatment of AIDS related conditions such as AIDS-related complex (ARC) and AIDS-related neurological conditions. The present invention is also useful in the prevention or the reduction of the likelihood of progression to clinical illness of individuals who are anti-HIV antibody or HIV-antigen positive and in prophylaxis following exposure to HIV.

The present invention may also be used in the treatment of HBV infections, including the use in combination with other anti-HBV agents for the treatment of acute or chronic HBV infections, especially including for example, lamivudine, Beta-L-5-Fluoro-2',3'-dideoxydidehydrocytidine (β-LFd4C), Beta-L-5-Fluoro-2', 3'-dideoxycytidine (β-LFddC) or other nucleoside anti-HBV agents. The invention is also useful in the prevention or the reduction of the likelihood of progression to clinical illness of individuals who are anti-HBV antibody or HBV-antigen positive and in prophylaxis following potential exposure to HBV such as after a liver transplant.

The present invention is also directed to the use of one or more compounds as otherwise described herein in combination with other anti-HSV agents for the treatment of HSV infections, especially for example, acyclovir (ACV). The invention is also useful in the prevention or the reduction of the likelihood of progression to clinical illness of individuals who are infected with HSV or in prophylaxis following potential exposure to HSV.

The present invention also relates to compositions and methods for use in treating fungal infections either alone or using combinations of agents. Suitable therapeutic agents for use in such combination include 3-AP, 3-AMP or one or more of its prodrug forms as described in detail hereinabove, alone or in combination with another anti-fungal agents such as terbinafine, fluconazole, itraconazole, posaconazole, clotrimazole, griseofulvin, nystatin, tolnaftate, caspofungin, amphotericin B, liposomal amphotericin B, and amphotericin B lipid complex.

In another aspect, the present invention is directed to the use of one or more compounds according to the present invention in a pharmaceutically acceptable carrier in combination with at least one other anti-viral agent at a suitable dose ranging from about 1 to about 100 mg/kg of body weight per day, preferably within the range of about 2 to 50 mg/kg/day, most preferably in the range of 3 to 20 mg/kg/day. The desired dose may conveniently be presented in a single dose or as divided doses administered at appropriate intervals, for example as two, three, four or more sub-doses per day.

Ideally, the active ingredient should be administered to achieve peak plasma concentrations of the active compound of from about 0.05 to about 5 uM, preferably about 0.1 to 2 uM, most preferably about 0.2 to about 1 uM. This may be achieved, for example, by the intravenous injection of about a 0.1 to 10% solution of the active ingredient, optionally in saline, or orally administered as a bolus containing about 0.1 to about 5 g of the active ingredient. Desirable blood levels may be maintained by a continuous infusion to preferably provide about 0.01 to about 2.0 mg/kg/hour or by intermittent infusions containing about 0.4 to about 15 mg/kg of the active ingredient. Oral dosages, where applicable, will depend on the pharmacokinetics of the compounds to be administered. While it is possible that, for use in therapy, a compound of the invention may be administered as the raw chemical it is preferable to present the active ingredient as a pharmaceutical formulation.

Pharmaceutical formulations include those suitable for oral, rectal, nasal, topical (including buccal and sub-lingual), vaginal or parenteral (including intramuscular, subcutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

When desired, the above described formulations may be adapted to provide sustained release characteristics of the active ingredient(s) in the composition.

In the pharmaceutical aspect according to the present invention, the compound(s) according to the present invention is formulated preferably in admixture with a pharmaceutically acceptable carrier. In general, it is preferable to administer the pharmaceutical composition parenterally and in particular, in intravenously or intramuscular dosage form, but a number of formulations may be administered via other parenteral routes, such as transdermal, buccal, subcutaneous, suppository or other route, including via an oral route of administration. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (such as salt formulation, etc.) which are well within the ordinary skill in the art. It is also well within the routineer's skill to modify the route of administration and dosage regimen of a particular compound in order to manage the pharmacokinetics of the present compounds for maximum beneficial effect to the patient.

The routineer will take advantage of favorable pharmacokinetic parameters of the pro-drug forms of the present invention, where applicable, in delivering the present compounds to a patient suffering from a viral infection to maximize the intended effect of the compound.

The pharmaceutical compositions according to the invention may also contain other active ingredients such as antimicrobial agents, antiinfective agents, or preservatives.

The invention thus provides, in a further aspect, a pharmaceutical composition combination comprising an effective amount of 3-AP, 3-AMP or one or more of its prodrug forms as otherwise described herein or a pharmaceutically acceptable derivative thereof together with another therapeutically active agent, and in particular, another antiviral agent. Effective amounts or concentrations of each of the active compounds are to be included within the pharmaceutical compositions according to the present invention.

Pharmaceutical formulations comprising at least one of 3-AP, 3-AMP and prodrug forms presented in combination with an effective amount of at least one additional anti-viral agent in further combination with a pharmaceutically acceptable carrier, represent a further aspect of the present invention.

The present invention also relates to compositions and methods for use in treating viral infections using combinations of agents. Suitable therapeutic agents for use in such combinations with 3-AP, 3-AMP or one or more of its prodrug forms include acyclic nucleosides such as acyclovir or ganciclovir, interferons such as alpha., beta or gamma.-interferon, reverse transcriptase inhibitors and nucleosides, transport inhibitors such as dipyridamole, 2',3'-dideoxynucleosides (including β-L-FddC), 2,3'-dideoxy-2', 3'-didehydronucleosides (including β-L-Fd4C), 3TC (lamivudine), AZT, 2',3'-dideoxycytidine (DDC), 2',3'-dideoxyadenosine, 2',3'-dideoxyinosine (DDI), 2',3'-dideoxythymidine (DDT), 2',3'-dideoxy-2',3'-didehydrothymidine (D4T) and 2',3'-dideoxy-2',3'-didehydrocytidine (D4C), tenofirir DF, adefovir, dipivoxil, immunomodulators such as interleukin II (IL2) and granulocyte macrophage colony stimulating factor (GM-CSF), erythropoetin, ampligen, thymodulin, thymopentin, foscarnet, ribavirin and inhibitors of HIV binding to CD4 receptors e.g. soluble CD4, CD4 fragments, CD4 hybrid molecules, glycosylation inhibitors such as 2-deoxy-D-glucose, castanospermine and 1-deoxynojirimycin.

The individual components of such combinations may be administered either sequentially or simultaneously in separate or combined pharmaceutical formulations.

When one or more of the compounds according to the present invention is used in combination with a second therapeutic agent active against the same virus or fungus the dose of each compound may be either the same as or differ from that when the compound is used alone. Appropriate doses will be readily appreciated by those skilled in the art.

Chemical Synthesis

Compositions according to the present invention are synthesized using the general and synthetic methods which are set forth in U.S. Pat. No. 5,767,134, issued Jun. 16, 1998 and as otherwise set forth herein. Additional prodrug forms of 3-AP and 3-AMP are synthesized by the methods which may be followed in the '134 patent as well as methods which are described below.

A number of phosphate bearing prodrugs (as set forth in FIG. 1) were synthesized readily in good quantities and evaluated. The disodium salts of these prodrugs were very soluble in water.

Figure 2:
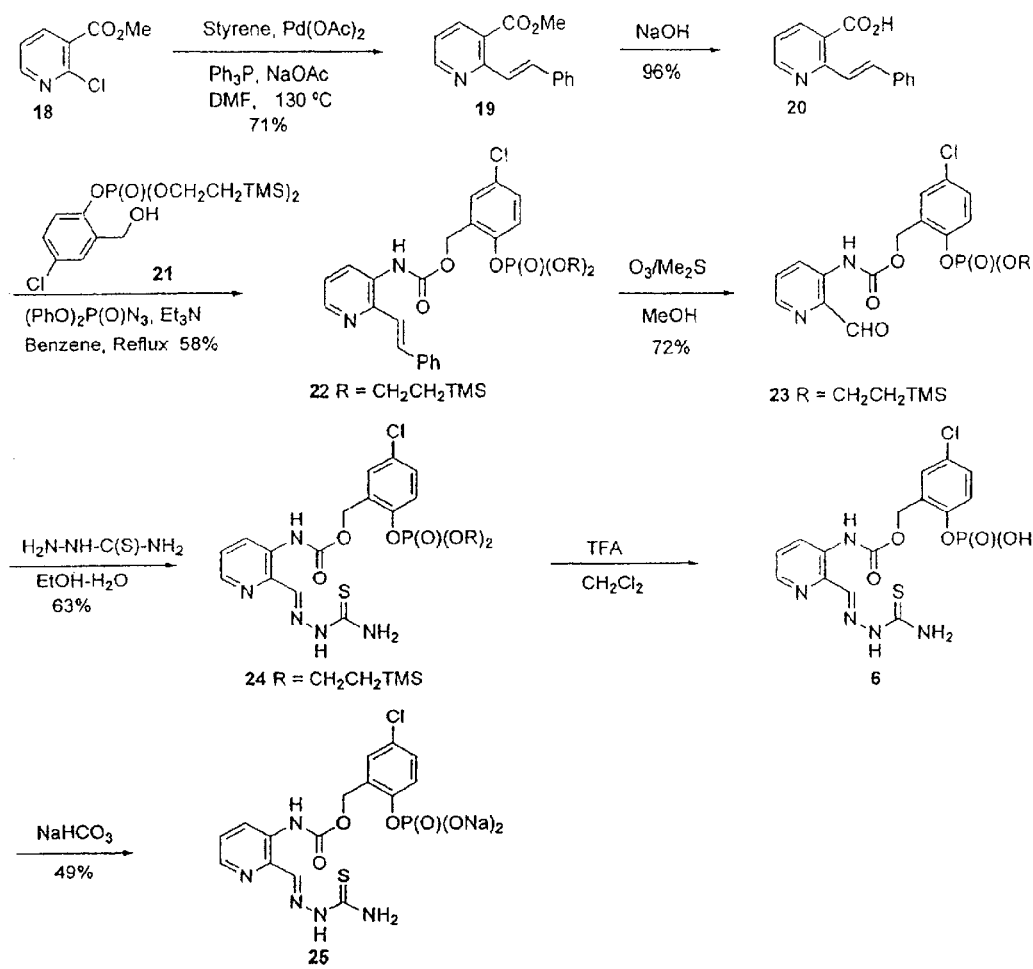
FIGS. 2–3 are representations of chemical schemes for synthesizing compounds according to the present invention.

As set forth in attached FIG. 2, the 5-chloro prodrug compound 6 was synthesized as shown. Thus, the acid 20 was prepared from, for example, 2-chloro-3-nicotinic acid methyl ester 18 or a related derivative in a two-step sequence consisting of a Heck reaction (See, Jeffery, *Tetrahedron* (1996), 52, 10113 and Dieck and Heck, *J. Org. Chem.* (1975), 40, 1083 and a NaOH promoted ester hydrolysis. The chloro ortho-phosphate linker 21 was prepared via an oxidative coupling between the bis-TMSE-phosphite (McCombie et al., *J. Chem. Soc.* (1945), 381) and 2-hydroxybenzyl alcohol. Initially, problems were encountered in the large-scale preparation of linker 21 as it decomposed during purification giving low yields. The conditions were standardized by using Et$_3$N as buffer to neutralize the acidity of silica gel to obtain the linker in good quantities (88%). Heating a reaction mixture consisting of the acid 20, the linker 21, triethylamine and diphenylphosphoryl azide under Curtius rearrangement conditions (Shipps et al., *J. Bioorg. Med. Chem.* (1996), 4, 655) provided the desired carbamate 22 (58%), which was converted sequentially to the aldehyde 23 (72%) and its corresponding thiosemicarbazone 24 in 63% yield. The removal of the 2-trimethylsilylethyl(TMSE) group in 24 was effected cleanly with TFA (Chao et al., *J. Org. Chem.* (1994), 59, 6687) and provided the 3-AP prodrug free acid 6, which was in turn converted to the disodium salt 25 upon treatment with saturated sodium bicarbonate solution and reverse phase column purification.

Figure 3:
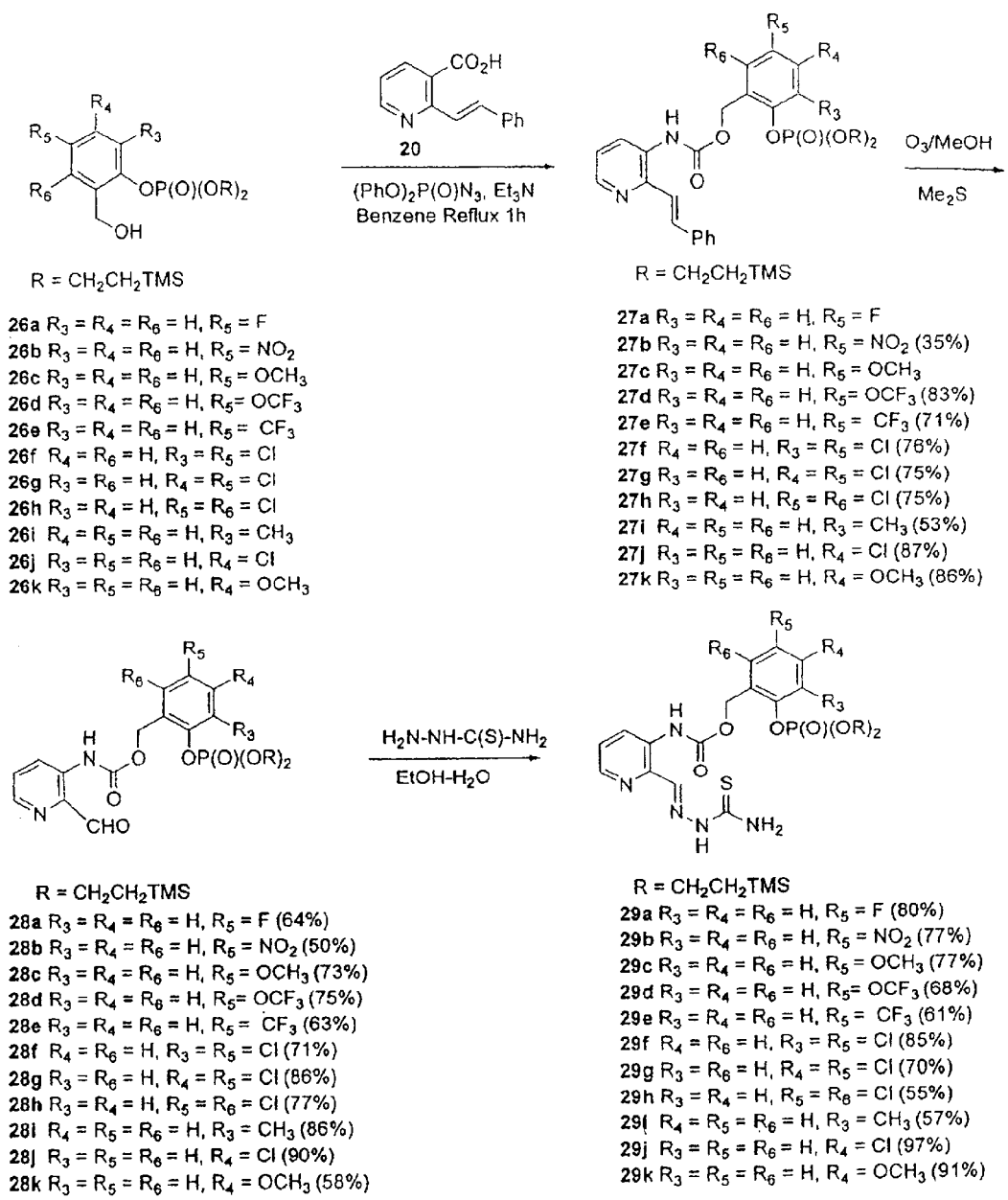

The other substituted ortho prodrugs were synthesized essentially following the same route using appropriate phosphate-bearing substituted benzyl linkers such as 21. Coupling of these linkers to 25, followed by functional group manipulations furnished the corresponding prodrugs (FIG. 3). The synthesis evidences that the prodrugs of the present invention may be readily converted to their corresponding phosphate salts. The water solubility of these phosphate salt compounds is excellent and is significantly greater than corresponding non-prodrug forms. The solubility of parental 3-AP in aqueous solution is less than 0.1 mg/ml, where as that of the prodrugs is between 16 and 35 mg/ml.

Having generally described the invention, reference is now made to the following specific examples which are intended to illustrate preferred and other embodiments and comparisons. The included examples are not to be construed as limiting the scope of this invention as is more broadly set forth above and in the appended claims.

All reagents were purchased at commercial quality and used without further purification, and solvents were dried and/or distilled before use where necessary. All NMR spectra ($^1$H, $^{13}$C, and $^{31}$P) were determined on a Brucker AC300 spectrometer. Chemical shifts are measured in parts per million (ppm) relative to tetramethylsilane. Coupling constants are reported in hertz (Hz). Flash column chromatography (FCC) was performed with Merck silica gel 60 (230–400 mesh), and pre-treated with triethylamine for all trimethylsilylethyl (TMSE) protected compounds. Reversed phase column chromatography (RPCC) was packed with CAT gel (Waters, preparative C18 125 Å, 55–105 μm), eluting with milli-Q de-ionized water.

EXAMPLES 1–3

General Procedures for Preparation of the Nicotinic Acid (20)

EXAMPLE 1

Preparation of 2-chloronicotinic acid methyl ester (18)

To a mixture of 2-chloronicotinic acid (Aldrich, 100.0 g, 0.63 mol) in 1,4-dioxane (500 mL) was added thionyl chloride (70 mL, 0.96 mol). The suspension was heated under reflux for 22 h with a gas trap to absorb hydrogen chloride gas. After evaporation of the solvent, the residue was dissolved in methanol (300 mL). To the solution was added dropwise triethylamine (TEA, 120 mL, 1.26 mol) at 0° C. over 2 h. The solvents were evaporated and the residue was suspended in ethyl acetate. The precipitate was removed by filtration. The filtrate was concentrated to afford the ester 18 (92.3 g, 86%) as an oil:

Rf(1:5 v/v ethyl acetate-hexane) 0.38. $^1$H NMR (300 MHz, CDCl$_3$) δ 8.53 (dd, 4.8 Hz, 1H), 8.19 (dd, 7.6 Hz, 1H), 7.37 (dd, 7.7 Hz, 1H) and 3.97 (s, 3H). $^{13}$C NMR (75 MHz, CDCl$_3$) δ 164.5, 151.6, 149.6, 140.0, 126.4, 121.9 and 52.5.

EXAMPLE 2

Preparation of 2-styrylnicotinic acid methyl ester (19)

To a solution of the ester 18 (48.8 g, 0.28 mol) in DMF (450 mL) was added styrene (165 mL, 1.42 mol), palladium acetate (6.5 g, 30 mmol), sodium acetate (47 g, 0.57 mol) and triphenyl phosphine (30 g, 0.11 mol). The mixture was heated under reflux for 22 h. The palladium-catalyst was removed by filtration through a Celite pad. The filtrate was concentrated under reduced pressure, and the residue was dissolved in a minimum amount of ethyl acetate. To the above solution was added hexane. After removal of the precipitate by filtration, the filtrate was concentrated. The resulting crude material was purified by FCC (1:1 v/v ethyl acetate-hexane) to afford the ester 19 (55.0 g, 81%) as a light yellow oil:

Rf (1 :5 v/v ethyl acetate-hexane) 0.41. $^1$H NMR (300 MHz, CDCl$_3$) δ 8.70 (dd, 1H), 8.10 (dd, 1H), 8.16 (d, 1H), 7.94 (d, 1H), 7.64 (d, 2H), 7.4–7.3 (m, 3H), 7.18 (dd, 1H) and 3.94 (s, 3H). $^{13}$C NMR (75 MHz, CDCl$_3$) δ 166.7, 155.3, 152.0, 138.6, 136.7, 135.9, 128.6, 128.5, 127.5, 124.8, 123.8, 121.3 and 52.4.

EXAMPLE 3

Preparation of 2-styrylnicotinic acid (20)

A solution of the ester 19 (55.0 g, 0.23 mol) in THF (100 mL) was treated with a 3 N NaOH solution (110 mL, 0.25 mol) for 21 h at ambient temperature. After removal of solvents, the residue was taken up in water and ethyl ether. The phases were separated, and the aqueous phase was washed with ether (2×). The resulting aqueous phase was neutralized with a 2 N HCl solution, and the precipitate was then collected by filtration to afford the acid 20 (50.2 g, 97%) as a cream solid:

$^1$H NMR (300 MHz, DMSO-d$_6$) δ 8.72 (dd, 1H), 8.19 (dd, 1H), 8.10 (d, 1H), 7.86 (d, 1H), 7.62 (d, 2H) and 7.4–7.3 (m, 4H). $^{13}$C NMR (75 MHz, DMSO-d$_6$) δ 167.9, 153.7, 151.8, 138.6, 136.4, 134.5, 128.9, 128.7, 127.2, 125.3 and 122.1.

EXAMPLES 4–5

General Procedures for Preparation of the Phosphate Linkers (21, 26a–k)

EXAMPLE 4

Preparation of bis(2-trimethylsilylethyl)phosphite (TMSE-phosphite)

To a solution of 2-(trimethylsilyl)ethanol (Aldrich, 25.0 g, 0.21 mol) in ethyl ether (200 mL) containing pyridine (11.4 mL, 0.14 mol) was added phosphorus trichloride (6.2 mL, 70 mmol) in one portion at –78° C. The reaction mixture was kept for 5 min while stirring, and then diluted with ethyl ether (500 mL). After warming to ambient temperature, the mixture was stirred for 18 h continually. The precipitate was removed by filtration, and the filtrate was then bubbled by ammonia gas for 10 min. The precipitate was removed by filtration through a Celite pad, and the filtrate was concentrated to afford TMSE-phosphite (20.7 g, 99%) as a colorless oil:

$^1$H NMR (300 MHz, CDCl$_3$) δ 6.76 (d, 1H), 4.13 (m, 4H), 1.07 (m, 4H) and 0.0 (s, 18H). $^{13}$C NMR (75 MHz, CDCl$_3$) δ 64.0 (d), 19.6 (d) and –1.6 (d). $^{31}$P NMR (121 MHz, CDCl$_3$) δ 18.5.

EXAMPLE 5

Preparation of 2-(TMSE-phosphonooxy)benzyl alcohols (21, 26a–k)

General Procedure. To a solution of the corresponding 2-hydroxybenzyl alcohol (10 mmol) in acetonitrile (40 mL) was added N,N'-diisopropylethylamine (DIEA, 11 mmol), 4-dimethylaminopyridine (DMAP, 1 mmol), and carbon tetrachloride (50 mmol). While stirring at –30° C., to the solution was added bis(2-trimethylsilylethyl)phosphite (stored in refrigerator, 11 mmol) immediately. After warming to ambient temperature, the reaction mixture was stirred for 3 h. The solvents were evaporated under reduced pressure, and the residual product was purified by FCC (1:1 v/v ethyl acetate-hexane) to afford the corresponding TMSE-protected phosphate linker (21, 26a–k).

2-Bis(2-trimethylsilylethyl)phosphonooxy-5-chlorobenzyl alcohol (21)

Following the above procedure, 5-chloro-2-hydroxybenzyl alcohol (5.0 g, 32 mmol) gave 21 (12.2 g, 88%) as an oil:

$^1$H NMR (300 MHz, CDCl$_3$) δ 7.33 (d, 1H), 7.11 (m, 1H), 7.02 (m, 1H), 4.49 (s, 2H), 4.12 (m, 4H), 1.00 (m, 4H) and –0.07 (s, 18H). $^{13}$C NMR (75 MHz, CDCl$_3$) δ 146.5 (d), 134.7 (d), 130.8, 130.2, 128.6, 122.0 (d), 67.7 (d), 59.4, 19.5 (d) and –1.6. $^{31}$P NMR (121 MHz, CDCl$_3$) δ 6.1.

2-Bis(2-trimethylsilylethyl)phosphonooxy-5-fluorobenzyl alcohol (26a).

Following the above procedure, 5-fluoro-2-hydroxybenzyl alcohol (17.0 g, 119 mmol) gave 26a (31.7 g, 62%) as an oil:

$^1$H NMR (300 MHz, CDCl$_3$) δ 7.2–7.1 (m, 1H), 7.0–6.9 (m, 1H), 4.63 (s, 1H), 4.3–4.1 (m, 4H), 1.2–1.1 (m, 4H) and 0.0 (s, 18H). $^{13}$C NMR (75 MHz, CDCl$_3$) δ 159.8 (d), 143.7 (dd), 135.2 (dd), 121.8 (dd), 116.4 (d), 115.0 (d), 67.6 (d), 59.4, 19.5 (d) and –1.6. $^{31}$P NMR (121 MHz, CDCl$_3$) δ 6.4. $^{19}$F NMR (282 MHz, CDCl$_3$) δ –59.8.

2-Bis(2-trimethylsilylethyl)phosphonooxy-5-nitrobenzyl alcohol (26b).

Following the above procedure, 2-hydroxy-5-nitrobenzyl alcohol (4.5 g, 27 mmol) gave 26b (6.4 g, 53%) as an oil:

$^1$H NMR (300 MHz, CDCl$_3$) δ 8.14 (m, 1H), 7.81 (m, 1H), 7.14 (m, 1H), 4.48 (s, 2H), 4.06 (m, 4H), 0.90 (m, 4H) and –0.20 (m, 18H). $^{13}$C NMR (75 MHz, CDCl$_3$) δ 152.0 (d), 144.6, 134.7 (d), 123.7, 123.4, 119.8, 67.9 (d), 58.4, 19.3 (d) and –1.6. $^{31}$P NMR (121 MHz, CDCl$_3$) δ 4.4.

2-Bis(2-trimethylsilylethyl)phosphonooxy-5-methoxybenzyl alcohol (26c).

Following the above procedure, 2-hydroxy-5-methoxybenzyl alcohol (11.0 g, 25 mmol) gave 26c (7.7 g, 70%) as an oil:

$^1$H NMR (300 MHz, CDCl$_3$) δ 7.06 (dd, 1H), 6.94 (d, 1H), 6.74 (dd, 1H), 4.57 (s, 2H), 4.3–4.1 (m, 4H), 3.74 (s, 3H), 1.1–1.0 (m, 4H) and 0.0 (m, 18H). $^{13}$C NMR (75 MHz, CDCl$_3$) δ 157.1, 141.7 (d), 134.0 (d), 121.9 (d), 125.3, 114.5, 67.5 (d), 60.2, 55.6, 19.6 (d) and –1.6. $^{31}$P NMR (121 MHz, CDCl$_3$) δ 6.9.

2-Bis(2-trimethylsilylethyl)phosphonooxy-5-trifluoromethoxybenzyl alcohol (26d).

Following the above procedure, 2-hydroxy-5-trifluoromethoxybenzyl alcohol (1.9 g, 9.1 mmol) gave 26d (3.3 g, 62%) as an oil:

$^1$H NMR (300 MHz, CDCl$_3$) δ 7.20 (d, 1H), 7.19 (dd, 1H), 7.09 (dd, 1H), 4.61 (s, 2H), 4.24 (m, 4H), 1.08 (m, 4H) and 0.0 (s, 18H). $^{13}$C NMR (75 MHz, CDCl$_3$) δ 146.4 (dd), 135.0 (d), 123.0, 122.1, 121.4, 67.8 (d), 59.6, 19.6 (d) and −1.6. $^{31}$P NMR (121 MHz, CDCl$_3$) δ 6.2. $^{19}$F NMR (282 MHz, CDCl$_3$) δ −58.7.

2-Bis(2-trimethylsilylethyl)phosphonooxy-5-trifluoromethylbenzyl alcohol (26e).

Following the above procedure, 2-hydroxy-5-trifluoromethylbenzyl alcohol (4.1 g, 22 mmol) gave 26e (7.9 g, 77%) as an oil:

$^1$H NMR (300 MHz, CDCl$_3$) δ 7.72 (br s, 1H), 7.51 (dd, 1H), 7.29 (d, 1H), 4.66 (s, 2H), 4.23 (m, 4H), 1.09 (m, 4H) and 0.0 (s, 18H). $^{13}$C NMR (75 MHz, CDCl$_3$) δ 150.6 (d), 133.8 (d), 127.7 (d), 126.1, 121.3 (d), 68.0 (d), 59.6, 19.6 (d) and −1.6. $^{31}$P NMR (121 MHz, CDCl$_3$) δ 5.8. $^{19}$F NMR (282 MHz, CDCl$_3$) δ −62.9.

2-Bis(2-trimethylsilylethyl)phosphonooxy-3,5-dichlorobenzyl alcohol (26f).

Following the above procedure, 3,5-dichloro-2-hydroxybenzyl alcohol (4.6 g, 24 mmol) gave 26f (7.2 g, 63%) as an oil:

$^1$H NMR (300 MHz, CDCl$_3$) δ 7.34 (d, 1H), 7.32 (dd, 1H), 4.56 (s, 2H), 4.25 (m, 4H), 1.08 (m, 4H) and 0.0 (s, 18H). $^{13}$C NMR (75 MHz, CDCl$_3$) δ 149.9, 143.3 (d), 136.9 (d), 131.2 (d), 129.9, 129.5, 127.6 (d), 68.3 (d), 59.8, 19.5 (d) and −1.6. $^{31}$P NMR (121 MHz, CDCl$_3$) δ 5.7.

2-Bis(2-trimethylsilylethyl)phosphonooxy-4,5-dichlorobenzyl alcohol (26g).

Following the above procedure, 4,5-dichloro-2-hydroxybenzyl alcohol (3.6 g, 18 mmol) gave 26g (5.2 g, 59%) as an oil:

$^1$H NMR (300 MHz, CDCl$_3$) δ 7.53 (s, 1H), 7.28 (s, 1H), 4.55 (s, 2H), 4.21 (m, 4H) 1.08 (m, 4H) and 0.0 (s, 18H). $^{13}$C NMR (75 MHz, CDCl$_3$) δ 146.6 (d), 133.5 (d), 131.9 (d), 131.6, 129.5 (d), 123.0 (d), 68.1 (d), 59.1, 19.6 (d) and −1.5. $^{31}$P NMR (121 MHz, CDCl$_3$) δ 6.0.

2-Bis(2-trimethylsilylethyl)phosphonooxy-5,6-dichlorobenzyl alcohol (26h).

Following the above procedure, 5,6-dichloro-2-hydroxybenzyl alcohol (4.8 g, 25 mmol) gave 26h (8.6 g, 73%) as an oil:

$^1$H NMR (300 MHz, CDCl$_3$) δ 7.35 (d, 1H), 7.04 (dd, 1H), 4.76 (s, 2H), 4.22 (m, 4H), 1.08 (m, 4H) and 0.0 (s, 18H). $^{13}$C NMR (75 MHz, CDCl$_3$) δ 147.6 (d), 134.7, 133.5 (d), 130.6 (d), 129.9, 120.8 (d), 68.1 (d), 57.3, 19.6 (d) and −1.6. $^{31}$P NMR (121 MHz, CDCl$_3$) δ 6.4.

2-Bis(2-trimethylsilylethyl)phosphonooxy-3-methylbenzyl alcohol (26i)

Following the above procedure, 2-hydroxy-3-methylbenzyl alcohol (2.0 g, 14 mmol) gave 26i (1.7 g, 88%) as an oil:

$^1$H NMR (300 MHz, CDCl$_3$) δ 7.16 (m, 1H), 7.0–6.9 (m, 2H), 4.48 (s, 2H), 4.13 (m, 4H), 2.22 (s, 3H), 0.97 (m, 4H) and −0.09 (s, 18H). $^{13}$C NMR (75 MHz, CDCl$_3$) δ 146.9 (d), 133.5 (d), 131.0, 130.4 (d), 129.4, 125.6 (d), 67.6 (d), 60.1, 19.5 (d), 16.8 and −1.6. $^{31}$P NMR (121 MHz, CDCl$_3$) δ 6.9.

2-Bis(2-trimethylsilylethyl)phosphonooxy-4-chlorobenzyl alcohol (26j).

Following the above procedure, 4-chloro-2-hydroxybenzyl alcohol (4.2 g, 26 mmol) gave 26j (9.6 g, 84%) as an oil:

R$_f$(4:1 v/v ethyl acetate-hexane) 0.67. $^1$H NMR (300 MHz, CDCl$_3$) δ 7.27 (d, 1H), 7.2–7.1 (m, 2H), 4.55 (s, 2H), 4.21 (m, 4H), 1.07 (m, 4H) and 0.0 (s, 18H). $^{13}$C NMR (75 MHz, CDCl$_3$) δ 148.5 (d), 133.9, 131.7 (d), 131.5, 126.0, 121.4 (d), 67.9 (d), 59.4, 19.5 (d) and −1.6. $^{-P\ NMR}$ (121 MHz, CDCl$_3$) δ 5.8.

2-Bis(2-trimethylsilylethyl)phosphonooxy-4-methoxybenzyl alcohol (26k).

Following the above procedure, 2-hydroxy-4-methoxybenzyl alcohol (2.7 g, 17 mmol) gave 26k (2.5 g, 33%) as an oil:

R$_f$ (4:1 v/v ethyl acetate-hexane) 0.70. $^1$H NMR (300 MHz, CDCl$_3$) δ 7.29 (d, 1H), 6.8–6.7 (m, 2H), 4.53 (s, 2H), 4.22 (m, 4H), 3.75 (s, 3H), 1.09 (m, 4H) and 0.0 (s, 18H). $^{13}$C NMR (75 MHz, CDCl$_3$) δ 160.1 (d), 149.1 (d), 131.9, 125.3 (d), 111.2, 107.3 (d), 67.6 (d), 59.7, 55.5, 19.6 (d) and −1.6. $^{31}$P NMR (121 MHz, CDCl$_3$) δ 6.4.

EXAMPLES 6–10

General Procedures for Preparation of the 3-AP Prodrugs (25, 30a–k)

EXAMPLE 6

Preparation of (2-styrylpyridin-3-yl)carbamic acid 2-(TMSE-phosphonooxy)benzyl esters (22, 27a–k)

(Curtius Rearrangement)

General Procedure. To a solution of 2-styrylnicotinic acid (20, 20 mmol) in benzene (100 mL) containing triethylamine (TEA, 32 mmol) was added diphenylphosphorylazide (32 mmol). The solution was heated at reflux for 10 min, and the corresponding TMSE-protected phosphate linker (21 or 26a–k, 20 mmol) was then added. The reaction mixture was kept under reflux for 3 h. Next, the solvents were evaporated under reduced pressure. The residual product was purified by FCC (1:4 v/v ethyl acetate-hexane) to afford the corresponding carbamate (22 or 27a–k).

(2-Styrylpyridin-3-yl)carbamic acid 2-bis(2-trimethylsilylethyl)phosphonooxy-5-chlorobenzyl ester (22).

Following the above procedure, 21 (9.4 g, 21 mmol) gave 22 (10.6 g, 58%) as an oil:

$^1$H NMR (300 MHz, CDCl$_3$) δ 8.23 (d, 1H), 7.92 (br s, 1H), 7.56 (d, 1H), 7.4–7.0 (m, 11H), 5.11 (s, 2H), 4.10 (m, 4H), 0.94 (m, 4H) and −0.14 (s, 18H). $^{13}$C NMR (75 MHz, CDCl$_3$) δ 153.7, 151.9, 147.3 (d), 146.8, 145.2, 136.5, 134.8, 131.4, 130.2, 129.5, 129.3, 129.2, 128.5, 128.3, 127.2, 122.3, 121.3, 121.2, 67.4 (d), 61.6, 19.4 (d) and −1.7. $^{31}$P NMR (121 MHz, CDCl$_3$) δ 5.1. Mass Calcd. For C$_{31}$H$_{42}$ClN$_2$O$_6$PSi$_2$: 661.277; Found: 661.2

(2-Styrylpyridin-3-yl)carbamic acid 2-bis(2-trimethylsilylethyl)phosphonooxy-5-fluorobenzyl ester (27a).

Following the above procedure, the cruse carbamate 27a obtained from 26a (31.0 g, 73 mmol) was directly used for the further reaction without purification.

(2-Styrylpyridin-3-yl)carbamic acid 2-bis(2-trimethylsilylethyl)phosphonooxy-5-nitrobenzyl ester (27b).

Following the above procedure, 26b (4.3 g, 9.6 mmol) gave 27b (2.3 g, 35%) as an oil:

$^1$H NMR (300 MHz, CDCl$_3$) δ 8.3–7.0 (m, 14H), 5.21 (s, 2H), 4.16 (m, 4H), 0.99 (m, 4H) and −0.12 (m, 18H). $^{13}$C NMR (75 MHz, CDCl$_3$) δ 153.5, 153.2 (d), 149.9, 145.6, 144.3, 136.4, 135.1, 131.1, 129.3, 129.0 (d), 128.5, 128.4, 127.2, 124.9, 124.8, 122.4, 120.9, 120.3, 68.0 (d), 62.1, 19.5 (d), 17.1 and −1.6. $^{31}$P NMR (121 MHz, CDCl$_3$) δ 4.5.

(2-Styrylpyridin-3-yl)carbamic acid 2-bis(2-trimethylsilylethyl)phosphonooxy-5-methoxybenzyl ester (27c).

Following the above procedure, the cruse carbamate 27c obtained from 26c (6.0 g, 26 mmol) was directly used for the further reaction without purification.

(2-Styrylpyridin-3-yl)carbamic acid 2-bis(2-trimethylsilylethyl)phosphonooxy-5-trifluoromethoxybenzyl ester (27d).

Following the above procedure, 26d (1.9 g, 8.5 mmol) gave 27d (3.4 g, 83%) as an oil:

$^1$H NMR (300 MHz, CDCl$_3$) δ 8.39 (dd, 1H), 8.13 (br s, 1H), 7.74 (d, 1H), 7.60 (m, 2H), 7.41 (dd, 1H), 7.4–7.1 (m, 7H), 5.30 (s, 2H), 4.27 (m, 4H), 1,10 (m, 4H) and 0.0 (s, 18H). $^{13}$C NMR (75 MHz, CDCl$_3$) δ 153.4, 147.3 (d), 145.7, 145.4, 136.6, 135.4, 131.2, 129.8, 129.7, 129.2 (d), 128.6, 128.5, 127.4, 127.0, 125.2, 122.7, 122.5, 122.2, 121.5, 120.8, 120.0 (d), 118.6, 67.6 (d), 62.0, 19.6 (d) and −1.6. $^{31}$P NMR (121 MHz, CDCl$_3$) δ 5.3. $^{19}$F NMR (282 MHz, CDCl$_3$) δ −58.7.

(2-Styrylpyridin-3-yl)carbamic acid 2-bis(2-trimethylsilylethyl)phosphonooxy-5-trifluoromethylbenzyl ester (27e).

Following the above procedure, 26e (5.1 g, 11 mmol) gave 27e (5.3 g, 71%) as an oil:

$^1$H NMR (300 MHz, CDCl$_3$) δ 8.40 (dd, 1H), 8.14 (br s, 1H), 7.74 (d, 2H), 7.6–7.5 (m, 4H), 7.4–7.1 (m, 8H), 5.29 (s, 2H), 4.29 (m, 4H), 1.11 (m, 4H) and 0.0 (s, 18H). $^{13}$C NMR (75 MHz, CDCl$_3$) δ 153.4, 145.4 (m), 136.5, 135.4, 131.1, 129.7, 128.6, 128.5, 128.2, 128.1, 127.4, 127.1 (d), 122.5, 120.8, 120.5, 120.0 (d), 67.7 (d), 61.9, 19.6 (d) and −1.6. $^{31}$P NMR (121 MHz, CDCl$_3$) δ 5.0. $^{19}$F NMR (282 MHz, CDCl$_3$) δ 62.7.

(2-Styrylpyridin-3-yl)carbamic acid 2-bis(2-trimethylsilylethyl)phosphonooxy-3,5-dichlorobenzyl ester (27f).

Following the above procedure, 26f (6.3 g, 13 mmol) gave 27f (7.1 g, 76%) as an oil:

$^1$H NMR (300 MHz, CDCl$_3$) δ 8.39 (dd, 1H), 8.11 (br s, 1H), 7.74 (d, 1H), 7.59 (br d, 2H), 7.4–7.2 (m, 8H), 7.18 (dd, 2H), 5.35 (s, 2H), 4.29 (m, 4H), 1.11 (m, 4H) and 0.0 (s, 18H). $^{13}$C NMR (75 MHz, CDCl$_3$) δ 153.3, 145.4 (d), 136.5, 135.4, 131.9 (d), 131.1, 131.0, 130.2, 129.8, 129.7, 128.7, 128.6, 128.3, 128.0 (d), 127.4, 122.5, 120.8, 67.9 (d), 62.2, 19.5 (d) and −1.6. $^{31}$P NMR (121 MHz, CDCl$_3$) δ 5.0.

(2-Styrylpyridin-3-yl)carbamic acid 2-bis(2-trimethylsilylethyl)phosphonooxy-4,5-dichlorobenzyl ester (27g).

Following the above procedure, 26g (11.3 g, 50 mmol) gave 27g (17.4 g, 75%) as an oil:

$^1$H NMR (300 MHz, CDCl$_3$) δ 8.38 (dd, 1H), 8.12 (br s, 1H), 7.74 (d, 1H), 7.60 (dd, 2H), 7.53 (s, 1H), 7.51 (d, 1H), 7.4–7.2 (m, 6H), 7.17 (dd, 2H), 5.23 (s, 2H), 4.27 (m, 4H), 1.10 (m, 4H) and 0.0 (s, 18H). $^{13}$C NMR (75 MHz, CDCl$_3$) δ 153.4, 147.7 (d), 145.4, 136.6, 135.4, 133.1, 131.3, 131.2, 128.9, 128.6, 128.5, 127.7 (d), 127.4, 122.5, 120.8, 67.8 (d), 61.5, 19.6 (d) and −1.6. $^{31}$P NMR (121 MHz, CDCl$_3$) δ 5.2.

(2-Styrylpyridin-3-yl)carbamic acid 2-bis(2-trimethylsilylethyl)phosphonooxy-5,6-dichlorobenzyl ester (27h).

Following the above procedure, 26h (6.2 g, 28 mmol) gave 27h (9.6 g, 75%) as an oil:

$^1$H NMR (300 MHz, CDCl$_3$) δ 8.38 (dd, 1H), 8.20 (br s, 1H), 7.73 (d, 1H), 7.60 (br d, 2H), 7.48 (d, 1H), 7.4–7.2 (m, 7H), 7.18 (dd, 2H), 5.48 (s, 2H), 4.28 (m, 4H), 1.10 (m, 4H) and 0.0 (s, 18H). $^{13}$C NMR (75 MHz, CDCl$_3$) δ 153.4, 149.2 (d), 145.2, 136.5, 135.4, 134.7, 131.3, 131.0, 129.8, 129.4, 128.6, 128.5, 127.4, 127.3 (d), 122.5, 120.7, 119.6 (d), 67.7 (d), 59.9, 19.6 (d) and −1.6. $^{31}$P NMR (121 MHz, CDCl$_3$) δ 5.0.

(2-Styrylpyridin-3-yl)carbamic acid 2-bis(2-trimethylsilylethyl)phosphonooxy-3-methylbenzyl ester (27i).

Following the above procedure, 26i (1.4 g, 6.2 mmol) gave 27i (1.5 g, 53%) as an orange oil:

$^1$H NMR (300 MHz, CDCl$_3$) δ 8.23 (dd, 1H), 7.97 (br s, 1H), 7.66 (m, 1H), 7.58 (d, 1H), 7.4–6.9 (m, 10H), 5.27 (s, 2H), 4.11 (m, 4H), 2.27 (s, 3H), 0.94 (m, 4H) and −0.11 (s, 18H). $^{13}$C NMR (75 MHz, CDCl$_3$) δ 153.9, 147.6 (d), 146.4, 145.1, 136.6, 134.7, 131.7, 131.6, 131.0, 130.8 (d), 128.5, 128.4 (d), 128.3, 127.6, 127.3, 125.3, 122.3, 121.2, 67.1 (d), 62.9, 19.5 (d), 17.1 and −1.6. $^{31}$P NMR (121 MHz, CDCl$_3$) δ 5.6. Mass Calcd. For C$_{32}$H$_{45}$N$_2$O$_6$PSi$_2$: 640.859; Found: 640.2

(2-Styrylpyridin-3-yl)carbamic acid 2-bis(2-trimethylsilylethyl)phosphonooxy-4-chlorobenzyl ester (27j).

Following the above procedure, 26j (9.3 g, 21 mmol) gave 27j (12.6 g, 87%) as an oil:

Rf(1:1 v/v ethyl acetate-hexane) 0.82. $^1$H NMR (300 MHz, CDCl$_3$) δ 8.28 (dd, 1H), 8.15 (br s, 1H), 7.72 (d, 1H), 7.60 (d, 2H), 7.4–7.3 (m, 7H), 7.2–7.1 (m, 2H), 5.26 (s, 2H), 4.28 (m, 4H), 1.11 (m, 4H) and 0.0 (s, 18H). $^{13}$C NMR (75 MHz, CDCl$_3$) δ 153.6, 149.7 (d), 145.2, 136.6, 135.3, 135.1, 131.4, 131.3, 128.6, 128.5, 127.4, 125.9 (d), 125.4, 122.4, 120.9 (d), 120.8, 67.6 (d), 62.1, 19.5 (d) and −1.6. $^{31}$P NMR (121 MHz, CDCl$_3$) δ 5.1.

(2-Styrylpyridin-3-yl)carbamic acid 2-bis(2-trimethylsilylethyl)phosphonooxy-4-methoxybenzyl ester (27k).

Following the above procedure, 26k (2.8 g, 6.5 mmol) gave 27k (3.7 g, 86%) as an oil:

Rf(1:1 v/v ethyl acetate-hexane) 0.50. $^1$H NMR (300 MHz, CDCl$_3$) δ 8.36 (dd, 1H), 8.18 (br s, 1H), 7.72 (d, 1H), 7.4–7.3 (m, 6H), 7.62 (d, 2H), 7.2–7.1 (m, 1H), 6.97 (m, 1H), 6.71 (dd, 1H), 5.24 (s, 2H), 4.29 (m, 4H), 3.80 (s, 3H), 1.11 (m, 4H) and 0.0 (s, 18H). $^{13}$C NMR (75 MHz, CDCl$_3$) δ 160.5, 153.9, 150.0 (d), 145.0, 136.7, 135.1, 131.9, 131.6, 130.0, 128.6, 128.4, 127.4, 122.4, 120.9, 119.2 (d), 110.4, 67.3 (d), 62.4, 55.5, 19.6 (d) and −1.6. $^{31}$P NMR (121 MHz, CDCl$_3$) δ 5.2.

EXAMPLE 7

Preparation of (2-formylpyridin-3-yl)carbamic acid 2-(TMSE-phosphonooxy)benzyl esters (23, 28a–k) (ozonolysis)

General Procedure. The corresponding 2-styrylpyridine (22 or 27a–k, 10 mmol) was dissolved in dichloromethane (50 mL) and ethanol (40 mL). The light yellow solution was ozonized at −50° C. till the solution turned to light blue. Nitrogen gas was bubbled through the solution for 30 min to expel excess ozone. To the solution was then added dimethyl sulfide (5 mL), and the mixture was stirred for 2 h at room temperature. The solvent was evaporated under reduced pressure, and the residual product was purified by FCC (1:9 v/v ethyl acetate-hexane) to afford the corresponding pyridine-2-carboxaldehyde (23 or 28a–k).

(2-Formylpyridin-3-yl)carbamic acid 2-bis(2-trimethylsilylethyl)phosphonooxy-5-chlorobenzyl ester (23).

Following the above procedure, 22 (2.4 g, 3.7 mmol) gave 23 (1.6 g, 72%) as an oil:

$^1$H NMR (300 MHz, CDCl$_3$) δ 10.38 (br s, 1H), 9.90 (s, 1H), 8.67 (d, 1H), 8.28 (dd, 1H), 7.4–7.3 (m, 2H), 7.23 (dd,

1H), 7.13 (dd, 1H), 5.14 (s, 2H), 4.12 (m, 4H), 0.97 (m, 4H) and −0.14 (m, 18H). $^{13}$C NMR (75 MHz, CDCl$_3$) δ 197.0, 152.9, 147.3 (d), 143.7, 138.3, 136.7, 130.1, 129.6, 129.5, 128.6, 128.5, 126.2, 121.3, 67.4 (d), 61.6, 19.4 (d) and −1.7. $^{31}$P NMR (121 MHz, CDCl$_3$) δ 5.1.

(2-Formylpyridin-3-yl)carbamic acid 2-bis(2-trimethylsilylethyl)phosphonooxy-5-fluorobenzyl ester (28a).

Following the above procedure, the crude 27a (31.0 g, 73 mmol) gave 28a (26.9 g, 64%) as an oil:
$^1$H NMR (300 MHz, CDCl$_3$) δ 10.58 (s, 1H), 10.10 (s, 1H), 8.86 (d, 1H), 8.48 (dd, 1H), 7.52 (m, 1H), 7.4–7.3 (m, 1H), 7.21 (dd, 1H), 7.1–6.9 (m, 1H), 5.30 (s, 2H), 4.4–4.2 (m, 4H), 1.2–1.0 (m, 4H) and 0.0 (s, 18H). $^{13}$C NMR (75 MHz, CDCl$_3$) δ 197.1, 159.3 (d), 152.9, 144.5 (dd), 143.7, 143.5, 138.4, 136.8, 121.4 (dd), 116.2 (d), 115.9 (d), 67.3 (d), 61.8,19.5 (d) and −1.6. $^{31}$P NMR (121 MHz, CDCl$_3$) δ 5.5. $^{19}$F NMR (282 MHz, CDCl$_3$) δ −59.3.

(2-Formylpyridin-3-yl)carbamic acid 2-bis(2-trimethylsilylethyl)phosphonooxy-5-nitrobenzyl ester (28b).

Following the above procedure, 27b (4.2 g, 9.4 mmol) gave 28b (2.8 g, 50%) as an oil:
$^1$H NMR (300 MHz, CDCl$_3$) δ 10.42 (br s, 1H), 9.89 (s, 1H), 8.64 (d, 1H), 8.28 (dd, 1H), 8.21 (d, 1H), 8.05 (dd, 1H), 7.47 (d, 1H), 7.33 (dd, 1H), 5.21 (s, 2H), 4.17 (m, 4H), 0.98 (m, 4H) and −0.13 (m, 18H). $^{13}$C NMR (75 MHz, CDCl$_3$) δ 197.0, 153.5 (d), 152.7, 144.3, 143.9, 138.1, 136.8, 128.6, 128.3 (d), 126.2, 125.4, 125.2, 120.3, 67.9 (d), 61.4, 19.5 (d) and −1.7. $^{31}$P NMR (121 MHz, CDCl$_3$) δ 4.5.

(2-Formylpyridin-3-yl)carbamic acid 2-bis(2-trimethylsilylethyl)phosphonooxy-5-methoxybenzyl ester (28c).

Following the above procedure, the crude 27c (7.5 g, 17 mmol) gave 28c (9.8 g, 73%) as an oil:
$^1$H NMR (300 MHz, CDCl$_3$) δ 10.37 (s, 1H), 9.93 (s, 1H), 8.71 (d, 1H), 8.30 (d, 1H), 7.34 (dd, 1H), 7.19 (d, 1H), 6.85 (d, 1H), 6.70 (d, 1H), 5.18 (s, 2H), 4.2–4.0 (m, 4H), 3.66 (s, 3H), 1.1–0.9 (m, 4H) and 0.0 (s, 18H). $^3$C NMR (75 MHz, CDCl$_3$) δ 196.9, 156.4, 153.1, 143.6, 142.4 (d), 138.5, 136.7, 128.6, 127.7 (d), 126.2, 120.9, 115.1, 114.3, 67.1 (d), 62.3, 55.5, 19.4 (d) and −1.7. $^{31}$P NMR (121 MHz, CDCl$_3$) δ 5.8.

(2-Formylpyridin-3-yl)carbamic acid 2-bis(2-trimethylsilylethyl)phosphonooxy-5-trifluoromethoxybenzyl ester (28d).

Following the above procedure, 27d (4.7 g, 6.6 mmol) gave 28d (3.2 g, 75%) as an oil:
$^1$H NMR (300 MHz, CDCl$_3$) δ 10.54 (br s, 1H), 10.06 (s, 1H), 8.82 (d, 1H), 8.44 (dd, 1H), 7.48 (dd, 1H), 7.44 (dd, 1H), 7.32 (d, 1H), 7.25 (s, 1H), 7.2-7.1 (m, 1H), 5.30 (s, 2H), 4.26 (m, 4H), 1.10 (m, 4H) and 0.0 (s, 18H). $^{13}$C NMR (75 MHz, CDCl$_3$) δ 197.2, 153.0, 147.1 (d), 145.7, 143.9, 138.4, 136.9, 129.8, 128.8, 128.7, 126.4, 122.6, 122.2, 121.3, 120.0, 119.9, 67.6 (d), 61.8, 19.5 (d) and −1.6. $^{31}$P NMR (121 MHz, CDCl$_3$) δ 5.3. $^{19}$F NMR (282 MHz, CDCl$_3$) δ −58.8.

(2-Formylpyridin-3-yl)carbamic acid 2-bis(2-trimethylsilylethyl)phosphonooxy-5-trifluoromethylbenzyl ester (28e).

Following the above procedure, 27e (12.2 g, 18 mmol) gave 28e (6.9 g, 63%) as an oil:
$^1$H NMR (300 MHz, CDCl$_3$) δ 10.54 (br s, 1H), 10.06 (d, 1H), 8.82 (br d, 1H), 8.44 (dd, 1H), 7.72 (br s, 1H), 7.6–7.5 (m, 2H), 7.48 (dd, 1H), 7.3–7.1 (m, 2H), 5.33 (s, 2H), 4.27 (m, 4H), 1.10 (m, 4H) and 0.0 (s, 18H). $^{13}$C NMR (75 MHz, CDCl$_3$) δ 197.1, 153.0, 151.5 (d), 143.9, 138.4, 136.9, 129.8, 129.7, 128.7, 127.7, 127.6, 127.3 (d), 127.1, 127.0, 126.4, 126.3, 125.2, 120.3 (d), 120.0 (d), 67.7 (d), 61.8, 19.6 (d) and −1.6. $^{31}$P NMR (121 MHz, CDCl$_3$) δ 4.9. $^{19}$F NMR (282 MHz, CDCl$_3$) δ −62.7.

(2-Formylpyridin-3-yl)carbamic acid 2-bis(2-trimethylsilylethyl)phosphonooxy-3,5-dichlorobenzyl ester (28f)

Following the above procedure, 27f (8.0 g, 12 mmol) gave 28f (5.1 g, 71%) as an oil:
$^1$H NMR (300 MHz, CDCl$_3$) δ 10.54 (br s, 1H), 10.05 (s, 1H), 8.79 (d, 1H), 8.42 (dd, 1H), 7.46 (dd, 1H), 7.35 (dd, 2H), 7.24 (s, 1H), 5.38 (s, 2H), 4.27 (m, 4H), 1.12 (m, 4H) and 0.0 (m, 18H). $^{13}$C NMR (75 MHz, CDCl$_3$) δ 197.2, 152.8, 149.9, 143.9, 143.6 (d), 138.4, 136.8, 131.8 (d), 131.0 (d), 130.1, 128.7, 128.0 (d), 127.8 (d), 126.3, 120.0 (d), 67.8 (d), 62.0, 19.6 (d) and −1.6. $^{31}$P NMR (121 MHz, CDCl$_3$) δ 5.1.

(2-Formylpyridin-3-yl)carbamic acid 2-bis(2-trimethylsilylethyl)phosphonooxy-4,5-dichlorobenzyl ester (28g).

Following the above procedure, 27g (17.4 g, 25 mmol) gave 28g (13.4 g, 86%) as an oil:
$^1$H NMR (300 MHz, CDCl$_3$) δ 10.51 (br s, 1H), 10.05 (s, 1H), 8.79 (d, 1H), 8.42 (dd, 1H), 7.53 (dd, 1H), 7.5–7.4 (m, 1H), 7.24 (s, 1H), 6.96 (dd, 1H), 5.23 (s, 2H), 4.28 (m, 4H), 1.10 (m, 4H) and 0.0 (m, 18H). $^{13}$C NMR (75 MHz, CDCl$_3$) δ 197.2, 152.9, 147.4 (d), 144.0, 138.3, 136.9, 133.1, 131.0, 128.8 (d), 128.7, 127.2 (d), 126.3, 122.2, 122.0, 67.8 (d), 61.3, 19.6 (d) and −1.6. $^{31}$P NMR (121 MHz, CDCl$_3$) δ 5.1.

(2-Formylpyridin-3-yl)carbamic acid 2-bis(2-trimethylsilylethyl)phosphonooxy-5,6-dichlorobenzyl ester (28h).

Following the above procedure, 27h (9.5 g, 14 mmol) gave 28h (6.5 g, 77%) as an oil: $^1$H NMR (300 MHz, CDCl$_3$) δ 10.44 (br s, 1H), 10.05 (s, 1H), 8.86 (d, 1H), 8.44 (dd, 1H), 7.50 (d, 1H), 7.47 (d, 1H), 7.41 (d, 1H), 7.38 (m, 1H), 5.46 (s, 2H), 4.25 (m, 4H), 1.10 (m, 4H) and 0.0 (m, 18H). $^{13}$C NMR (75 MHz, CDCl$_3$) δ 197.0, 153.0, 149.9, 149.2 (d), 143.8, 138.5, 136.8, 135.0, 131.2, 129.8, 129.6, 128.7, 126.6 (d), 126.3, 119.5 (d), 67.7 (d), 59.9, 19.5 (d) and −1.6. $^{31}$P NMR (121 MHz, CDCl$_3$) δ 4.9.

(2-Formylpyridin-3-yl)carbamic acid 2-bis(2-trimethylsilylethyl)phosphonooxy-3-methylbenzyl ester (28i).

Following the above procedure, 27i (1.5 g, 2.2 mmol) gave 28i (1.1 g, 86%) as an oil:
$^1$H NMR (300 MHz, CDCl$_3$) δ 10.35 (br s, 1H), 9.92 (s, 1H), 8.71 (d, 1H), 8.28 (dd, 1H), 7.32 (dd, 1H), 7.16 (d, 1H), 7.05 (d, 1H), 6.96 (dd, 1H), 5.31 (s, 2H), 4.12 (m, 4H), 2.28 (s, 3H), 0.97 (m, 4H) and −0.12 (m, 18H). $^{13}$C NMR (75 MHz, CDCl$_3$) δ 196.9, 153.2, 147.2 (d), 143.6, 138.6, 136.6, 131.6, 130.9 (d), 128.6, 128.0 (d), 127.4, 126.2, 125.3, 67.1 (d), 62.9, 19.4 (d), 17.0 and −1.7. $^{31}$P NMR (121 MHz, CDCl$_3$) δ 5.8.

(2-Formylpyridin-3-yl)carbamic acid 2-bis(2-trimethylsilylethyl)phosphonooxy-4-chlorobenzyl ester (28j).

Following the above procedure, 27j (12.2 g, 19 mmol) gave 28j (8.9 g, 80%) as an oil:
Rf (1:1 v/v ethyl acetate-hexane) 0.66. $^1$H NMR (300 MHz, CDCl$_3$) δ 10.49 (br s, 1H), 10.04 (s, 1H), 8.80 (d, 1H), 8.42 (dd, 1H), 7.5–7.4 (m, 3H), 7.16 (dd, 1H), 5.26 (s, 2H), 4.27 (m, 4H), 1.11 (m, 4H) and 0.0 (s, 18H). $^{13}$C NMR (75 MHz, CDCl$_3$) δ 197.1, 153.1, 149.3 (d), 143.8, 138.5, 136.8, 135.0, 131.0, 128.7, 126.3, 125.3 (d), 125.2, 120.5 (d), 67.5 (d), 61.9, 19.5 (d) and −1.6. $^{31}$P NMR (121 MHz, CDCl$_3$) δ 5.0.

(2-Formylpyridin-3-yl)carbamic acid 2-bis(2-trimethylsilylethyl)phosphonooxy-4-methoxybenzyl ester (28k).

Following the above procedure, 27k (5.1 g, 8.0 mmol) gave 28k (2.7 g, 58%) as an oil:

Rf(1:1 v/v ethyl acetate-hexane) 0.44. $^1$H NMR (300 MHz, CDCl$_3$) δ 10.50 (br s, 1H), 10.05 (s, 1H), 8.84 (d, 1H), 8.42 (dd, 1H), 7.46 (dd, 1H), 7.36 (dd, 1H), 7.01 (s, 1H), 6.71 (dd, 1H), 5.24 (s, 2H), 4.27 (m, 4H), 3.80 (s, 3H), 1.10 (m, 4H) and 0.0 (s, 18H). $^{13}$C NMR (75 MHz, CDCl$_3$) δ 197.0,160.9,153.4, 150.2 (d), 143.6,138.7, 136.7,131.7, 128.7, 126.3, 118.5 (d), 110.6, 106.1 (d), 67.3 (d), 62.4, 55.5, 19.5 (d) and −1.6. $^{31}$P NMR (121 MHz, CDCl$_3$) δ 5.0.

EXAMPLE 8

Preparation of pyridine–2-carboxaldehyde thiosemicarbazones (24, 29a–k)

General Procedure. The corresponding pyridine-2-formaldehyde (23 or 28a-k, 10 mmol) was dissolved in ethanol-water (2:1 v/v, 150 mL). To the solution was added thiosemicarbazide (11 mmol). The solution was stirred for 30 min at ambient temperature. After addition of water (50 mL), the reaction mixture was stirred vigorously for 2 h at room temperature. The yellow precipitate was collected by filtration, washed with ethanol-water (1:4 v/v) and dried in vacuum to afford the corresponding pyridine-2-carboxaldehyde thiosemicarbazone (24, 29a–k).

(2-Thiosemicarbazonomethylpyridin-3-yl)carbamic acid 2-bis(2-trimethyl silyl ethyl) phosphonooxy-5-chlorobenzyl ester (24).

Following the above procedure, 23 (6.9 g, 12 mmol) gave 24 (4.9 g, 63%) as a yellow solid:

$^1$H NMR (300 MHz, DMSO-d$_6$) δ 11.77 (br s, 1H), 10.03 (br s, 1H), 8.40 (dd, 1H), 8.28 (br s, 1H), 8.26 (s, 1H), 7.94 (br s, 1H), 7.5–7.4 (m, 4H), 5.20 (s, 2H), 4.06 (m, 4H), 0.98 (m, 4H) and −0.03 (m, 18H). $^{13}$C NMR (75 MHz, DMSO-d$_6$) δ 178.5, 153.4, 148.0 (d), 144.2, 142.9, 141.0, 133.9, 129.5 (d), 128.9, 128.4, 128.0, 124.4, 121.6, 65.1 (d), 61.2, 18.9 (d) and −1.5. $^{31}$P NMR (121 MHz, DMSO-d$_6$) δ 9.8. Mass Calcd. For C$_{25}$H$_{39}$ClN$_5$O$_6$PSSi$_2$: 660.267; Found:660.2

(2-Thiosemicarbazonomethylpyridin-3-yl)carbamic acid 2-bis(2-trimethylsilylethyl) phosphonooxy-5-fluorobenzyl ester (29a).

Following the above procedure, 28a (14.3 g, 25 mmol) gave 29a (12.9 g, 80%) as a yellow solid:

$^1$H NMR (300 MHz, DMSO-d$_6$) δ 11.85 (s, 1H), 10.13 (s, 1H), 8.45 (d, 1H), 8.26 (s, 1H), 7.5–7.1 (m, 5H), 5.21 (s, 2H), 4.2–4.0 (m, 4H), 1.0–0.9 (m, 4H) and 0.0 (s, 18H). $^{13}$C NMR (75 MHz, DMSO-d$_6$) δ 178.6, 159.8, 156.0, 153.4, 145.1 (d), 143.5, 141.5, 140.4, 134.2, 129.5, 124.5, 121.4 (d), 115.5, 64.4 (d), 61.3, 18.9 (d) and −1.6. $^{31}$P NMR (121 MHz, DMSO-d$_6$) δ 10.5. $^{19}$F NMR (282 MHz, DMSO-d$_6$) δ −62.5. Mass Calcd. For C$_{25}$H$_{39}$FN$_5$O$_6$PSSi$_2$: 643.813 Found:644.2

(2-Thiosemicarbazonomethylpyridin-3-yl)carbamic acid 2-bis(2-trimethylsilylethyl) phosphonooxy-5-nitrobenzyl ester (29b).

Following the above procedure, 28b (1.6 g, 2.7 mmol) gave 29b (1.3 g, 77%) as a yellow solid:

$^1$H NMR (300 MHz, DMSO-d$_6$) δ 11.86 (br s, 1H), 10.14 (br s, 1H), 8.4–8.2 (m, 4H), 7.87 (br s, 2H), 7.64 (m, 1H), 7.52 (m, 1H), 5.26 (s, 2H), 4.05 (m, 4H), 0.97 (m, 4H) and −0.03 (m, 18H). $^{13}$C NMR (75 MHz, DMSO-d$_6$) δ 178.6, 155.3 (d), 153.4, 143.7, 142.7, 140.7, 134.1, 128.1 (d), 125.2, 124.6, 124.5, 120.1, 64.8 (d), 61.2, 18.9 (d) and −1.5. $^{31}$P NMR (121 MHz, DMSO-d$_6$) δ 9.2.

(2-Thiosemicarbazonomethylpyridin-3-yl)carbamic acid 2-bis(2-trimethylsilylethyl) phosphonooxy-5-methoxybenzyl ester (29c).

Following the above procedure, 28c (5.0 g, 8.8 mmol) gave 29c (4.4 g, 77%) as a yellow solid:

$^1$H NMR (300 MHz, DMSO-d$_6$) δ 11.85 (s, 1H), 10.08 (s, 1H), 8.41 (d, 1H), 8.35 (d, 1H), 8.30 (s, 1H), 8.03 (s, 2H), 7.51 (dd, 1H), 7.26 (d, 1H), 7.01 (d, 1H), 6.90 (dd, 1H), 5.26 (s, 2H), 4.2–4.0 (m, 4H), 3.75 (s, 3H), 1.1–0.9 (m, 4H) and 0.0 (s, 18H). $^{13}$C NMR (75 MHz, DMSO-d$_6$) δ 178.7, 155.7, 153.6, 143.9, 142.6 (d), 134.2, 129.4, 128.4 (d), 124.5, 121.1, 114.1, 113.9, 64.9 (d), 61.9, 55.6,19.1 (d) and −1.4. $^{31}$P NMR (121 MHz, DMSO-d$_6$) δ 10.3. Mass Calcd. For C$_{26}$H$_{42}$N$_5$O$_7$PSSi$_2$: 655.848 Found:656.2

(2-Thiosemicarbazonomethylpyridin-3-yl)carbamic acid 2-bis(2-trimethylsilylethyl) phosphonooxy-5-trifluoromethoxybenzyl ester (29d).

Following the above procedure, 28d (2.5 g, 3.9 mmol) gave 29d (1.9 g, 68%) as a yellow solid:

$^1$H NMR (300 MHz, DMSO-d$_6$) δ 11.81 (s, 1H), 10.04 (br s, 1H), 8.42 (d, 1H), 8.26 (s, 1H), 7.95 (br s, 1H), 7.5–7.2 (m, 4H), 5.24 (s, 2H), 4.07 (m, 4H), 0.96 (m, 4H) and −0.04 (m, 18H). $^{13}$C NMR (75 MHz, DMSO-d$_6$) δ 178.4, 153.4, 147.8 (d), 144.1, 144.0, 133.9, 129.4 (d), 124.4, 121.9, 121.7, 121.6, 121.4, 118.3, 65.1 (d), 61.2, 18.9 (d) and −1.6. $^{31}$P NMR (121 MHz, DMSO-d$_6$) δ 9.8. $^{19}$F NMR (282 MHz, DMSO-d$_6$) δ −53.0.

(2-Thiosemicarbazonomethylpyridin-3-yl)carbamic acid 2-bis(2-trimethylsilylethyl) phosphonooxy-5-trifluoromethylbenzyl ester (29e).

Following the above procedure, 28e (5.3 g, 8.5 mmol) gave 29e (3.6 g, 61%) as a yellow solid:

$^1$H NMR (300 MHz, DMSO-d$_6$) δ 11.81 (s, 1H), 10.03 (br s, 1H), 8.42 (d, 1H), 8.4–8.3 (m, 2H), 8.26 (s, 1H), 7.89 (br s, 1H), 7.79 (s, 1H), 7.75 (d, 2H), 7.56 (d, 2H), 7.49 (dd, 1H), 5.27 (s, 2H), 4.06 (m, 4H), 0.97 (m, 4H) and −0.04 (m, 18H). $^{31}$P NMR (121 MHz, DMSO-d$_6$) δ 9.5. $^{19}$F NMR (282 MHz, DMSO-d$_6$) δ −56.2.

(2-Thiosemicarbazonomethylpyridin-3-yl)carbamic acid 2-bis(2-trimethylsilylethyl) phosphonooxy-3,5-dichlorobenzyl ester (29f).

Following the above procedure, 28f (4.8 g, 7.7 mmol) gave 29f (4.6 g, 85%) as a yellow solid: $^1$H NMR (300 MHz, DMSO-d$_6$) δ 11.75 (s, 1H), 10.04 (s, 1H), 8.39 (d, 1H), 8.30 (d, 1H), 8.26 (s, 1H), 7.91 (br s, 1H), 7.69 (dd, 1H), 7.50 (d, 1H), 7.43 (dd, 1H), 5.29 (s, 2H), 4.24 (m, 4H), 1.03 (m, 4H) and −0.01 (m, 18H). $^{31}$P NMR (121 MHz, DMSO-d$_6$) δ 10.3.

(2-Thiosemicarbazonomethylpyridin-3-yl)carbamic acid 2-bis(2-trimethylsilylethyl) phosphonooxy-4,5-dichlorobenzyl ester (29g).

Following the above procedure, 28g (2.0 g, 3.2 mmol) gave 29g (1.5 g, 70%) as a yellow solid:

$^1$H NMR (300 MHz, DMSO-d$_6$) δ 11.85 (s, 1H), 10.08 (s, 1H), 8.42 (d, 1H), 8.31 (d, 1H), 8.26 (s, 1H), 7.89 (m, 1H), 7.70 (s, 1H), 7.59 (s, 1H), 7.5–7.2 (m, 2H), 5.18 (s, 2H), 4.02 (m, 4H), 0.95 (m, 4H) and 0.0 (m, 18H). $^{13}$C NMR (75 MHz, DMSO-d$_6$) δ 178.6, 153.3, 148.8, 143.8, 142.4, 140.6, 134.0, 130.8, 130.2 (d), 129.5, 128.3 (d), 125.8 (d), 124.4, 121.5, 119.9, 64.9 (d), 60.8, 18.9 (d) and −1.5. $^{31}$P NMR (121 MHz, DMSO-d$_6$) δ 9.7.

(2-Thiosemicarbazonomethylpyridin-3-yl)carbamic acid 2-bis(2-trimethylsilylethyl) phosphonooxy-5,6-dichlorobenzyl ester (29h).

Following the above procedure, 28h (5.9 g, 9.5 mmol) gave 29h (3.6 g, 55%) as a yellow solid:

$^1$H NMR (300 MHz, DMSO-d$_6$) δ 11.82 (s, 1H), 9.97 (br s, 1H), 8.50 (m, 1H), 8.41 (d, 1H), 8.27 (d, 1H), 8.23 (s, 1H), 7.72 (m, 1H), 7.67 (d, 1H), 7.48 (m, 1H), 7.41 (d, 1H), 7.3–7.1 (m, 1H), 5.32 (s, 2H), 4.03 (m, 4H), 0.96 (m, 4H) and −0.06 (m, 18H). $^{13}$C NMR (75 MHz, DMSO-d$_6$) δ 178.3, 153.3, 150.6 (d), 143.8, 140.8, 134.0, 133.8, 133.3, 131.2, 130.3, 129.4, 126.7 (d), 124.4, 120.1, 119.9 (d), 64.8 (d), 59.4, 18.9 (d) and −1.6. $^{31}$P NMR (121 MHz, DMSO-d$_6$) δ 9.6.

(2-Thiosemicarbazonomethylpyridin-3-yl)carbamic acid 2-bis(2-trimethylsilylethyl) phosphonooxy-3-methylbenzyl ester (29i).

Following the above procedure, 28i (1.1 g, 1.9 mmol) gave 29i (0.7 g, 57%) as a yellow solid:

$^1$H NMR (300 MHz, DMSO-d$_6$) δ 11.76 (br s, 1H), 9.99 (br s, 1H), 8.42 (br s, 1H), 8.37 (m, 1H), 8.27 (br s, 1H), 8.24 (m, 1H), 8.03 (br s, 1H), 7.45 (dd, 1H), 7.25 (d, 1H), 7.19 (d, 1H), 7.11 (dd, 1H), 5.30 (s, 2H), 4.08 (m, 4H), 2.29 (s, 3H), 1.01 (m, 4H) and −0.13 (m, 18H). $^{13}$C NMR (75 MHz, DMSO-d$_6$) δ 178.7, 153.8, 147.5 (d), 144.4, 143.2, 141.2, 134.3, 131.1, 130.7 (d), 128.9 (d), 126.4, 124.9, 124.6, 65.4 (d), 62.4, 19.2 (d), 16.9 and −1.4. $^{31}$P NMR (121 MHz, DMSO-d$_6$) δ 10.4.

(2-Thiosemicarbazonomethylpyridin-3-yl)carbamic acid 2-bis(2-trimethylsilylethyl) phosphonooxy-4-chlorobenzyl ester (29j).

Following the above procedure, 28j (10.5 g, 18.5 mmol) gave 29j (11.8 g, 97%) as a yellow solid:

$^1$H NMR (300 MHz, DMSO-d$_6$) δ 11.74 (s, 1H), 10.05 (br s, 1H), 8.4–8.3 (m, 3H), 7.85 (br s, 1H), 7.56 (d, 1H), 7.5–7.4 (m, 3H), 5.21 (s, 2H), 4.22 (m, 4H), 1.04 (m, 4H) and −0.01 (s, 18H). $^{13}$C NMR (75 MHz, DMSO-d$_6$) δ 153.2, 148.5, 148.4, 144.8, 144.5, 133.8, 133.0, 130.8, 126.5, 126.4, 125.4, 124.1, 119.7, 67.2 (d), 60.8, 18.9 (d) and −1.6. $^{31}$P NMR (121 MHz, DMSO-d$_6$) δ 9.5.

(2-Thiosemicarbazonomethylpyridin-3-yl)carbamic acid 2-bis(2-trimethylsilylethyl) phosphonooxy-4-methoxybenzyl ester (29k).

Following the above procedure, 28k (2.6 g, 4.5 mmol) gave 29k (2.7 g, 91%) as a yellow solid:

$^1$H NMR (300 MHz, DMSO-d$_6$) δ 11.74 (d, 1H), 9.98 (br s, 1H), 8.4–8.3 (m, 3H), 7.82 (br s, 1H), 7.44 (m, 1H), 6.87 (m, 3H), 5.16 (s, 2H), 4.19 (m, 4H), 3.77 (s, 3H), 1.03 (m, 4H) and −0.01 (s, 18H). $^{13}$C NMR (75 MHz, DMSO-d$_6$) δ 178.4, 160.0, 153.2, 150.2, 148.4, 144.8, 144.5, 133.8, 133.0, 130.8, 124.1, 119.0, 110.4, 106.0, 66.8 (d), 61.4, 55.3, 18.9 (d) and −1.6. $^{31}$P NMR (121 MHz, DMSO-d$_6$) δ 9.6.

EXAMPLE 9

Preparation of free phosphonic acids (6–17)

General Procedure. To a solution of the corresponding TMSE-protected phosphate (24 or 29a–k, 10 mmol) in dichloromethane (300–500 mL) was added trifluoroacetic acid (TFA, 20–50 mL) at 0° C. The reaction mixture was stirred vigorously for 2 h in an ice bath. A precipitate was collected by filtration, washed with cold dichloromethane, and then dried in vacuum. More commonly, the solvents were evaporated, and the resulting residual mixture was then dried in vacuum. The corresponding free phosphonic acid (6–17) was obtained as a yellow solid or glassy solid.

EXAMPLE 10

Preparation of disodium salt of phosphonic acid (25, 30a–k)

General Procedure. The corresponding free phosphonic acid (6–17, 10 mmol) was neutralized with an aqueous saturated sodium bicarbonate (NaHCO$_3$) solution (50–100 mL). The suspension was stirred for 2 h at ambient temperature, and then added a minimum amount of water to make homogenous. The aqueous solution was purified by reversed phase column chromatography with de-ionized water. The fractions were monitored by $^{31}$P NMR and combined. After lyophilization, the corresponding disodium salt (25 or 30a–k) was obtained as a pale yellow powder.

(2-Thiosemicarbazonomethylpyridin-3-yl)carbamic acid 2-(disodium phosphonooxy)-5-chlorobenzyl ester (25).

Following the above procedure, 24 (1.1 g, 1.7 mmol) gave 25 (0.4 g, 49%) as a pale yellow powder:

$^1$H NMR (300 MHz, D$_2$O) δ 7.94 (br s, 2H), 7.72 (s, 1H), 7.2–7.0 (m, 3H) and 4.98 (s, 2H). $^{13}$C NMR (75 MHz, D$_2$O) δ 179.6, 157.0, 153.2, 147.2 (d), 145.2, 136.8, 131.4, 130.5, 128.8, 127.8, 123.6 and 65.4. $^{31}$P NMR (121 MHz, D$_2$O) δ 14.3.

(2-Thiosemicarbazonomethylpyridin-3-yl)carbamic acid 2-(disodium phosphonooxy)-5-fluorobenzyl ester (30a)

Following the above procedure, 29a (10.5 g, 16 mmol) gave 7 (6.2 g, 86%), which upon treatment with NaHCO$_3$ gave 30a (4.0 g, 59%) as a pale yellow powder:

$^1$H NMR (300 MHz, D$_2$O) δ 8.2 (br s, 1H), 7.8 (br m, 1H), 7.57 (br s, 1H), 7.15 (m, 1H), 6.93 (m, 1H), 6.81 (m, 1H), 6.78 (m, 1H) and 4.93 (s, 2H). $^{13}$C NMR (75 MHz, D$_2$O) δ 179.4, 161.5, 158.4, 156.5, 150.3, 147.3, 146.5, 136.7, 130.8, 130.4, 127.7, 123.5, 117.5, 117.2 and 65.2. $^{31}$P NMR (121 MHz, D$_2$O) δ 14.5. $^{19}$F NMR (282 MHz, D$_2$O) δ −57.4.

(2-Thiosemicarbazonomethylpyridin-3-yl)carbamic acid 2-(disodium phosphonooxy)-5-nitrobenzyl ester (30b).

Following the above procedure, 29b (2.1 g, 3.0 mmol) gave 30b (1.0 g, 73%) as a dark yellow powder:

$^1$H NMR (300 MHz, D$_2$O) δ 8.0–7.8 (m, 4H), 7.40 (m, 1H), 7.17 (m, 1H) and 5.06 (s, 2H). $^{31}$P NMR (121 MHz, D$_2$O) δ 13.8.

(2-Thiosemicarbazonomethylpyridin-3-yl)carbamic acid 2-(disodium phosphonooxy)-5-methoxybenzyl ester (30c).

Following the above procedure, 29c (4.3 g, 16 mmol) gave 9 (2.9 g, 98%), which upon treatment with NaHCO$_3$ gave 30c (1.6 g, 43%) as a pale yellow powder:

$^1$H NMR (300 MHz, D$_2$O) δ 7.96 (br s, 1H), 7.70 (br s, 1H), 7.21 (br s, 1H), 7.08 (br s, 1H), 6.73 (s, 2H), 5.05 (s, 2H) and 3.65 (s, 3H). $^{13}$C NMR (75 MHz, D$_2$O) δ 174.5, 151.8, 151.1, 143.4, 142.1, 141.7, 135.9, 131.6, 126.4, 124.9, 122.6, 118.4, 111.7, 60.8 and 53.2. $^{31}$P NMR (121 MHz, D$_2$O) δ 14.6.

(2-Thiosemicarbazonomethylpyridin-3-yl)carbamic acid 2-(disodium phosphonooxy)-5-trifluoromethoxybenzyl ester (30d).

Following the above procedure, 29d (1.9 g, 2.6 mmol) gave 30d (0.5 g, 31%) as a pale yellow powder:

$^1$H NMR (300 MHz, D$_2$O) δ 7.93 (br s, 1H), 7.86 (br d, 1H), 7.71 (s, 1H), 7.25 (d, 1H), 7.02 (m, 4H) and 5.01 (s, 2H). $^{13}$C NMR (75 MHz, D$_2$O) δ 179.5, 173.5, 157.1, 153.3, 147.1, 146.8, 145.5, 141.2 (m), 136.5, 132.4 (m), 130.2 (d), 127.7 (d), 124.5, 124.0, 123.1, 122.6, 121.0 and 65.4. $^{31}$P NMR (121 MHz, D$_2$O) δ 14.3. $^{19}$F NMR (282 MHz, D$_2$O) δ −56.3.

(2-Thiosemicarbazonomethylpyridin-3-yl)carbamic acid 2-(disodium phosphonooxy)-5-trifluoromethylbenzyl ester (30e).

Following the above procedure, 29e (3.6 g, 5.2 mmol) gave 30e (1.3 g, 45%) as a pale yellow powder:

$^1$H NMR (300 MHz, D$_2$O) δ 7.98 (br s, 1H), 7.89 (d, 1H), 7.77 (s, 1H), 7.4–7.3 (m, 3H), 7.08 (m, 1H) and 5.04 (s, 2H). $^{31}$P NMR (121 MHz, D$_2$O) δ 14.0. $^{19}$F NMR (282 MHz, D$_2$O) δ −59.4.

(2-Thiosemicarbazonomethylpyridin-3-yl)carbamic acid 2-(disodium phosphonooxy)-3,5-dichlorobenzyl ester (30f).
Following the above procedure, 29f (4.5 g, 6.5 mmol) gave 30f (0.8 g, 24%) as a pale yellow powder:

$^1$H NMR (300 MHz, D$_2$O) δ 8.31 (br s, 1H), 7.88 (br d, 2H), 7.6–7.5 (m, 2H), 7.2–6.8 (m, 5H) and 5.07 (s, 2H). $^{13}$C NMR (75 MHz, D$_2$O) δ 179.6, 156.6 (d), 149.4 (d), 147.4, 146.8 (d), 136.6, 134.2, 131.5, 131.1, 130.7 (d), 130.1, 128.5, 127.7 (d) and 65.6. $^{31}$P NMR (121 MHz, D$_2$O) δ 14.4.

(2-Thiosemicarbazonomethylpyridin-3-yl)carbamic acid 2-(disodium phosphonooxy)-4,5-dichlorobenzyl ester (30g).
Following the above procedure, 29g (2.5 g, 3.0 mmol) gave 30g (0.4 g, 23%) as a pale yellow powder:

$^1$H NMR (300 MHz, D$_2$O) δ 8.07 (s, 1H), 7.99 (m, 1H), 7.85 (s, 1H), 7.39 (s, 1H), 7.19 (m, 2H) and 4.99 (s, 2H). $^{31}$P NMR (121 MHz, D$_2$O) δ 14.3.

(2-Thiosemicarbazonomethylpyridin-3-yl)carbamic acid 2-(disodium phosphonooxy)-5,6-dichlorobenzyl ester (30h).
Following the above procedure, 29h (4.6 g, 6.6 mmol) gave 30h (2.3 g, 64%) as a pale yellow powder:

$^1$H NMR (300 MHz, D$_2$O) δ 8.01 (s, 1H), 7.91 (br s, 1H), 7.73 (s, 1H), 7.23 (dd, 2H), 7.12 (m, 1H) and 5.18 (s, 2H). $^{31}$P NMR (121 MHz, D$_2$O) δ 14.2.

(2-Thiosemicarbazonomethylpyridin-3-yl)carbamic acid 2-(disodium phosphonooxy)-3-methylbenzyl ester (30i).
Following the above procedure, 29i (1.2 g, 1.8 mmol) gave 30i (0.5 g, 57%) as a yellow powder:

$^1$H NMR (300 MHz, D$_2$O) δ 8.11 (br s, 2H), 7.91 (m, 2H), 7.71 (m, 1H), 7.00 (m, 2H), 6.84 (m, 1H), 5.22 (s, 2H) and 2.14 (s, 3H). $^{13}$C NMR (75 MHz, D$_2$O) δ 146.1, 134.6, 133.6, 131.1, 128.8, 127.9, 125.7, 66.6 and 19.1. $^{31}$P NMR (121 MHz, D$_2$O) δ 14.2.

(2-Thiosemicarbazonomethylpyridin-3-yl)carbamic acid 2-(disodium phosphonooxy)-4-chlorobenzyl ester (30j).
Following the above procedure, 29j (4.2 g, 6.6 mmol) gave 30j (1.6 g, 48%) as a pale yellow powder:

$^1$H NMR (300 MHz, D$_2$O) δ 7.98 (s, 1H), 7.90 (m, 1H), 7.74 (s, 1H), 7.31 (s, 1H), 7.09 (m, 3H), 6.85 (m, 1H) and 5.00 (s, 2H). $^{13}$C NMR (75 MHz, D$_2$O) δ 180.0, 157.7, 155.9, 147.6, 147.4, 142.3, 137.1, 136.8, 133.2, 132.9, 128.3, 127.9, 124.9 and 65.9. $^{31}$P NMR (121 MHz, D$_2$O) δ 14.3.

(2-Thiosemicarbazonomethylpyridin-3-yl)carbamic acid 2-(disodium phosphonooxy)-4-methoxybenzyl ester (30k).
Following the above procedure, 29k (2.9 g, 4.4 mmol) gave 30k (1.2 g, 54%) as a pale yellow powder:

$^1$H NMR (300 MHz, D$_2$O) δ 8.06 (s, 1H), 7.94 (s, 1H), 7.64 (s, 1H), 7.13 (m, 1H), 7.0–6.8 (m, 3H), 6.43 (m, 1H), 4.06 (s, 2H) and 3.58 (s, 3H). $^{13}$C NMR (75 MHz, D$_2$O) δ 161.5, 161.3, 155.1, 133.1, 127.3, 127.0, 111.4, 108.3 and 57.9. $^{31}$P NMR (121 MHz, D$_2$O) δ 14.3.

BIOLOGICAL DATA—EXAMPLE 11

Antiviral Activity of Triapine (R$^1$ and R$^2$ are both H) Plus Lamivudine Against HIV-1 Infection MT-2 cells infected with strain IIIB of HIV (wildtype, 3TC resistant, or AZT resistant) are used for determining antiviral activities (Bridges et al., *Biochem. Pharmacol.* Vol. 51, 731–36, 1996). Cells are infected with virus at a multiplicity of infection of 0.1 TCID$_{50}$/ml and added to wells containing serial 2-fold dilutions of drugs. MT-2 cells in RPMI 1640 medium supplemented with 10% dialyzed fetal bovine serum and 100 μg/mL Kanamnycin are infected with virus and immediately added to serial dilutions of the drugs. After 5 days, 20 μL of MTT dye (2.5 mg/mL in PBS) is added per well. At the end of the 4-h incubation period, 150 μL of acidified 2-propanol with 2% NP-40 nonionic detergent is added per well. After the crystals of dye are dissolved (usually 1–2 days), the plates are read on a microplate reader. Using this MTT-dye reduction method (Larder et al., (1990), Antimicrob. Agents Chemother. 34, 436–41), the percentage of protection can be calculated from the formula [(a−b)/(c−b)×100] in which a is the A$_{595}$ of drug-treated virus-infected wells, b is the A$_{595}$ of no-drug infected cells, and c is the A$_{595}$ of the no-drug uninfected cells. The EC$_{50}$ was calculated from linear log 10 plots of the percentage protection verses inhibition concentration. Concentrations of Triapine tested are ranging from 0.1 to 0.8 micromolar where concentration of lamivudine are from 0.02 to 2 micromolar.

EXAMPLE 12

Figure 4:
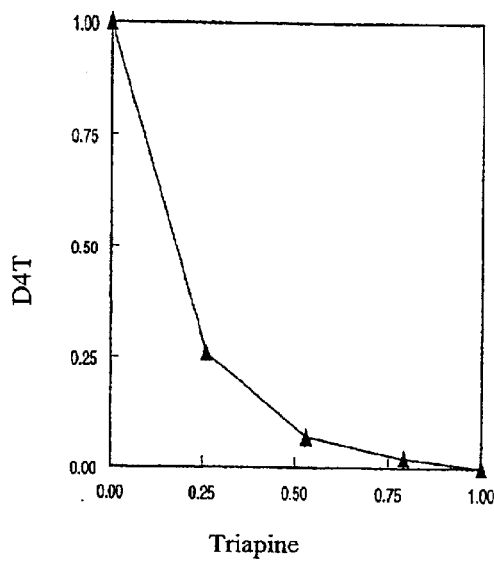
FIG. 4 depicts the antiviral activity of combinations of Triapine with D4T, ddI and AZT.
Figure 4:
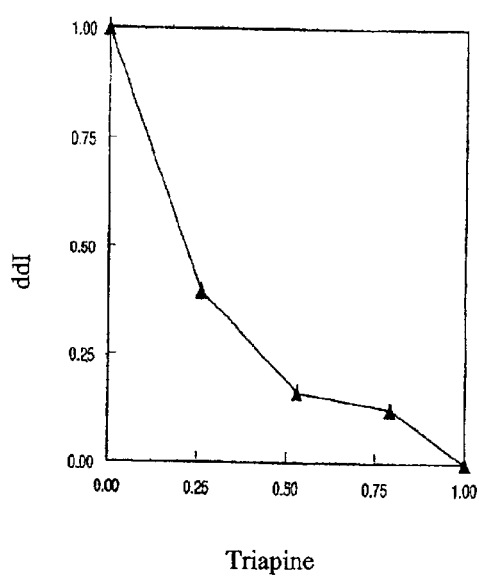
Figure 4:
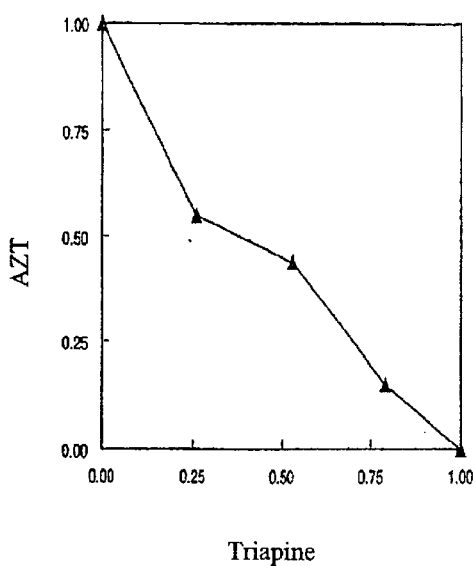

Antiviral Activity of Triapine (R$^1$ and R$^2$ are both H) Plus D4T, DDI and AZT Against HIV-1 Infection Using the above-described experimental system, the ability of Triapine to potentiate the anti-HIV activity of the dideoxynucleoside analogs ddI (2',3'-dideoxyinosine), D4T (2',3'-dideoxydidehydrothymidine) and AZT (3'-azidothymidine) was examined in HIV-infected MT-2 cells (as described above). Isobolograms, describing the interactions, were plotted according to the method described in Bridges et al., *Biochem. Pharmacol.*, 51, 731–736 (1996). The results, presented in FIG. 4, evidence that triapine elicits synergistic anti-HIV activites when combined with D4T and ddI and interacts in an additive fashion when combined with AZT.

EXAMPLE 13

Antiviral Activity of Triapine Plus Lamivudine Against HBV Infection

The effects of drugs on HBV viral DNA replication are assessed as described by Doong et al. (*Proc. Natl. Acad. Sci. USA* 88, 8495–99, 1991). A human hepatoma cell line carrying HBV (designated 2.2.15) is used in this study (Price et al., (1989) *Proc. Natl. Acad. Sci. USA* 86, 8541–44). Six-day-old cultures are treated with various concentrations of the drug in culture medium (minimal essential medium with Earle's salts and 10% fetal bovine serum [MEME]). The drugs are left in the culture medium for 3 days, and then the medium is aspirated and fresh medium containing the same concentration of the drugs are added. At the end of the subsequent 3-day period, the culture medium is harvested. An aliquot of the culture medium (5 μl) is used for the estimation of the HBV surface antigen (HBVsAg) (as described below). The culture medium is processed to obtain virions by polyethylene glycol precipitation. The viral DNA recovered from the secreted particles is subjected to Southern blot analysis (Sambrook et al., (1989) Molecular cloning laboratory manual, 2nd ed. Cold Spring Harbor Laboratory, Cold Spring Harbor, N.Y.). Inhibition of viral DNA replication is determined by comparison of the viral DNAs from drug-treated and nontreated cultures. Southern blot analysis of the DNA is performed, and the level of inhibition is determined by hybridization of the blots to an HBV-specific probe followed by autoradiography. Quantitation of the autoradiographs is performed by densitometric scans on a densitometer. The percentage of inhibition can be calculated from the formula [1−(a−b)/(c−b)×100] in which a is the densitometric unit of drug-treated virus-infected wells, b is the densitometric unit of no-drug infected cells, and c is the densitometric unit of the no-drug uninfected cells. The ED$_{50}$ was calculated from linear log 10 plots of percentage inhibition verses the inhibition concentration.

EXAMPLE 14

Antiviral Activity of Triapine Plus Acyclovir Against HSV Infection

To evaluate the antiviral activities of Triapine, acyclovir, and combination thereof, HeLa $S_3$ cells are seeded in 25-cm$^2$ flasks and are used as host cells for virus infection (laboratory strains of virus HSV-1, HSV-2, wild type (Darby et al., (1982) *Nature,* 289, 81–3; Cheng, et al., *Antimicrob. Agents Chemother.* 18, 957–61, 1980). After a 1-hr adsorption period with virus at 5–10 plaque-forming units per cell, the monolayers are rinsed with phosphate-buffered saline, followed by the addition of 5 ml of growth medium containing various concentrations of drug. Concentrations of Triapine tested range from 0.1 to 1.0 micromolar where concentrations of acyclovir are from 1–50 micromolar. The cells are incubated at 37° C. for 48 hr and then are stored frozen at −70° C. until titration. The amounts of HSV contained in cells are determined with Vero cells using the methods described by Cheng et al. (Cheng, et al., *Antimicrob. Agents Chemother.* 18, 957–61, 1980).

The results of the above-test are presented in the following Table 1, below, which presents the antiviral activity of Triapine, at low, non-toxic clinically achievable concentrations of 0.3, 0.6 and 1.0 μM, in combination with acyclovir against HSV-1 (KOS) and HSV-2 (333) strains of herpes simplex virus in a virus yield assay. The experimental results evidence that in the presence of as little as 0.3 and 0.6 μM Triapine, the $EC_{90}$ of ACV decreased by 10-to greater than 24-fold for HSV-1. A greater than 4-fold decrease in the $EC_{90}$ of ACV against HSV-2 is observed with 0.6 μM Triapine. These data evidence that Triapine may markedly potentiate the anti-HSV activity of anti-HSV nucleoside-type analogs such as ACV in treating HSV infections.

TABLE 1

Virus Yield Assay in HSV-Infected Vero Cells

| DRUG | $EC_{90}$ (μM) | |
|---|---|---|
| | HSV-1 | HSV-2 |
| ACV | 29.3 | 36.5 |
| Triapine | >1 | >1 |
| 0.3 ACV + 0.3 μM Triapine | 2.9 | 4.7 |
| 0.6 ACV + 0.6 μM Triapine | 1.2 | 4.8 |
| ACV + 1.0 μM Triapine | <0.005 | 2.2 |

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A method of treating an HIV infection in a patient in need thereof comprising administering to said patient in combination, an effective amount of at least one compound according to the structure:

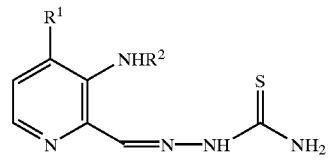

Where $R^1$ and $R^2$ are both H, with an effective amount of at least one anti-HIV agent selected from the group consisting of ddI and D4T, said administration producing a synergistic effect in treating said patient.

2. The method according to claim 1 wherein said anti-HIV agent is ddI.

3. The method according to claim 1 wherein said anti-HIV agent is D4T.

4. A method of treating an HSV infection in a patient in need thereof comprising administering in combination, an effective amount of at least one compound according to the structure:

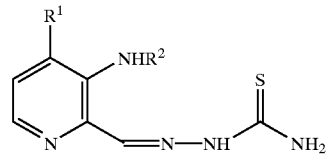

Where $R^1$ and $R^2$ are both H, with an effective amount of acyclovir.

* * * * *